US011794126B2

(12) United States Patent
Maconi et al.

(10) Patent No.: US 11,794,126 B2
(45) Date of Patent: Oct. 24, 2023

(54) SYSTEM, APPARATUSES, DEVICES, AND METHODS FOR PRODUCING PARTICLES

(71) Applicant: Nanoform Finland PLC, Helsinki (FI)

(72) Inventors: Goran Maconi, Helsinki (FI); Pia Runeberg-Roos, Espoo (FI); Daniel Veira Canle, Helsinki (FI); Kari Seppälä, Helsinki (FI); Maria Lume, Helsinki (FI); Edward Haeggstrom, Helsinki (FI)

(73) Assignee: NANOFORM FINLAND PLC, Helsinki (FI)

( * ) Notice: Subject to any disclaimer, the term of this patent is extended or adjusted under 35 U.S.C. 154(b) by 0 days.

(21) Appl. No.: 17/974,490

(22) Filed: Oct. 26, 2022

(65) Prior Publication Data

US 2023/0048148 A1 Feb. 16, 2023

Related U.S. Application Data

(63) Continuation of application No. PCT/EP2021/082722, filed on Nov. 23, 2021.

(60) Provisional application No. 63/117,898, filed on Nov. 24, 2020.

(51) Int. Cl.

| | |
|---|---|
| ***B01D 1/18*** | (2006.01) |
| ***B01J 2/04*** | (2006.01) |
| ***A61K 9/14*** | (2006.01) |

(52) U.S. Cl.
CPC .................. *B01D 1/18* (2013.01); *A61K 9/14* (2013.01); *B01J 2/04* (2013.01)

(58) Field of Classification Search
CPC .................................... B01D 1/18; A61K 9/14
See application file for complete search history.

(56) References Cited

U.S. PATENT DOCUMENTS

| | | | | |
|---|---|---|---|---|
| 2017/0333861 | A1 | 11/2017 | Friesen et al. | |
| 2020/0247702 | A1* | 8/2020 | Yuan | C02F 1/06 |
| 2020/0261930 | A1 | 8/2020 | Liu et al. | |

FOREIGN PATENT DOCUMENTS

| | | | |
|---|---|---|---|
| CN | 109 433 123 | A | 3/2019 |
| CN | 210 868 279 | U | 6/2020 |
| WO | WO 2020/092721 | A2 | 5/2020 |

OTHER PUBLICATIONS

English machine translation of CN 1094333123 (Year: 2019).*
International Search Report and Written Opinion issued for PCT/EP2021/082722 dated May 3, 2022, 16 pages.

* cited by examiner

*Primary Examiner* — Renee Robinson
(74) *Attorney, Agent, or Firm* — COOLEY LLP

(57) ABSTRACT

Embodiments of the present disclosure include, for example, systems, apparatuses, devices, and methods for producing a population of particles. In some embodiments, such particles include particles corresponding to an active, pharmaceutical ingredient.

23 Claims, 21 Drawing Sheets

SYSTEM, APPARATUSES, DEVICES, AND METHODS FOR PRODUCING PARTICLES

RELATED APPLICATIONS

This application is a continuation of PCT/EP2021/082722, filed Nov. 23, 2021, which claims benefit of and priority to U.S. provisional patent application no. 63/117,898, filed Nov. 24, 2020. Each of the entire foregoing disclosures is herein incorporated by reference in its entirety.

FIELD OF THE DISCLOSURE

The subject disclosure is directed to systems, devices, and methods for producing a plurality of particles of a predetermined size.

BACKGROUND

For biological pharmaceuticals ('biologics'), there are several methods for producing sub-micron sized particles. Many of these methods include inconvenient temperature ranges (spray drying), prolonged processing time (freeze-drying), and other stress factors (i.e., mechanical stress caused by milling) that may all affect the quality of the product.

Accordingly, what is needed is a system and method to produce a plurality of particles from biological material with at least one of, and preferably, two or more, and most preferably, all of a small particle size (smaller than 500 nm), narrow particle size distribution (PSD), a high yield, and retained biological activity.

SUMMARY

The subject disclosure addresses the issues of current particle producing systems and methods. Specifically, in some embodiments of the present disclosure, a particle generating apparatus for producing a plurality of particles of a predetermined size is provided, which includes atomization means, a connector, a drying chamber, at least one ionizer, and an electrostatic collector.

In many embodiments of the present disclosure, various flows are included and described, which can comprise at least one of a gas (e.g., air), a liquid, solid matter. Thus, upon a flow being described for some embodiments as an "airflow", one skilled in the art will appreciate that such is a fluid flow, and thus, can be a liquid flow as well.

In such embodiments, at least one of the following additional features, functionality, structure, steps, and/or clarifications (and in some embodiments, a plurality of, and in some embodiments, a majority of, substantially all of, and in some embodiments, all of) can be included, leading to yet further embodiments of the present disclosure:

- a solution container configured to retain a solution including at least one predetermined dissolved substance (PS) at a predetermined concentration;
- at least one pump configured to move at least one of the solution from a/the solution container to the atomization means and optionally return solution to the solution container;
- a scale configured to monitor solution consumption;
- the atomization means, which can also be referred to as an atomizer, and which also can be referred to as nebulizing means or a nebulizer (such terms and phrases are used interchangeably throughout this disclosure) can comprise at least one of a pneumatic atomizer (which can also be referred to as a pneumatic nebulizer) and an ultrasonic atomizer (which can also be referred to as an ultrasonic nebulizer), each configured to atomize the solution to produce a droplet flow comprising a plurality of droplets of the solution;
  - the atomizer means can further comprise a fluid (e.g., air or gas, which may be referred to as air or fluid, such terms are used interchangeably throughout this disclosure) inlet configured to provide air for the droplet flow;
  - in the pneumatic atomizer, at least one of a size and/or mass of the droplets and a flowrate thereof can be determined by a configuration of the design of the atomizer, and/or a driving airflow pressure of the atomization nebulizer (which can, in some embodiments, be referred to as a nozzle); and/or
  - in the ultrasonic atomizer, at least one of: a size and/or mass of the droplets and a flowrate thereof, can be determined by at least one of: one or more ultrasonic parameters comprising frequency, amplitude, and/or phase, duty cycle, and design of an atomizer vessel;
- the drying chamber can be configured to expose the droplet flow to a drying flow so as to produce a dried particle flow having particles of a size less than a predetermined threshold size (in some embodiments, approximately 50 nm, in some embodiments less than 1 mm);
- the drying chamber is configured to direct the dried particle flow with particles of a size less than or equal to a predetermined threshold;
- the drying chamber can include a drying chamber air inlet configured to supply air for the drying flow at a regulated flowrate to regulate at least one of the volume of the droplets and volume of dried particles;
- the drying chamber can further include a fan (and/or pump, such terms used interchangeably) configured to provide a constant pressure to the drying flow;
- the drying chamber can further include a drying chamber outlet;
- the drying chamber can further include a heater;
- the drying chamber can further include a laminar flow device(s) configured to generate a predetermined homogenous drying flow;
- the drying chamber can be configured to provide a controlled upward directed flow of the drying flow so as to dry the received droplet flow to form the plurality of dried particles;
- the drying chamber can be configured or further configured such that droplets over a predetermined or preselected size and/or mass travel downward against the drying flow, or are carried more slowly along the drying flow;
- in the drying chamber, droplets over the predetermined size and/or mass can be at least one of collected, and disposed of;
- the connector includes a bottom end, a top end, and a conduit connecting the first and second ends;
- the connector includes a connector droplet flow inlet;
- the connector can be configured such that a/the first end is arranged downstream from a/the second end and receives the droplet flow from an atomization means;
- with respect to the connector:
  - a/the conduit of the connector can include at least two turns forming at least one corresponding S-bend preventing a direct line of sight between the atomization means and the drying chamber inlet (and may be referred to, in some embodiments, as a staircase connector);

the second end includes a/the connector droplet flow outlet, which in some embodiments, corresponds to or otherwise comprises a/the drying chamber inlet; and/or a/the connector outlet (which in some embodiments corresponds to a/the drying chamber inlet) can be configured to at least one of shape and split the droplet flow into a plurality of flows;

at least one ionizer can comprise a plurality of ionizers;

the at least one ionizer is arranged and/or configured to expose the particle flow received from a/the drying chamber via the drying chamber outlet;

the at least one ionizer is configured to produce a temporally, preselected or predetermined ionized flow of negative ions configured to charge the particles of the particle flow to produce a charged particle flow;

the electrostatic collector can be configured to operate at a predetermined voltage, in some embodiments, between: 5 kV and 40 kV, 10 kV and 30 kV, 15 and 20 kV, and ranges between any of the foregoing, the electrostatic collector can be configured to receive the charged particle flow;

the electrostatic collector includes a central ground electrode protected by a glass tube, an external cylinder having a wall with a surface at the predetermined voltage, and/or an electrostatic collector outlet;

the electrostatic collector is configured to deflect the incoming charged particles of the charged particle flow towards the surface of the wall, where, deflected particles can form a predetermined or preselected layer on the surface of the wall (e.g., multiple layers, and/or 2D or 3D layers);

an electrostatic precipitator, such as any of multiple known, available electrostatic precipitator systems, can be used in place of an ionizer as an electrostatic collector;

an exhaust assembly;

an exhaust assembly, which may include one or more of:

an apparatus exhaust filter, which can be configured to capture dried particles from a/the electrostatic exhaust that are not collected in the electrostatic collector; and an apparatus exhaust arranged to exhaust a remaining flow of the apparatus;

at least one of the droplet flow, the drying flow, the dried particle flow, and the charged particle flow comprise corresponding airflows;

an atomization fuselage;

an atomization fuselage configured as an enclosed and/or airtight container for housing the atomization means;

an atomization fuselage including an inlet configured to receive a designated airflow; 5 and 20 L/min, 6 and 18 L/min, 7 and 16 L/min, 8 and 14 L/min, 9 and 12 L/min, 10 and 11 L/min, 10.5 L/min, and ranges between any of the foregoing;

an atomization fuselage including a tube routed through a portion (e.g., top, bottom or side thereof) of the fuselage;

an atomization fuselage configured to direct a least one filtered gas to the atomization means (e.g., the at least one gas comprises nitrogen);

at least one gas is supplied to an atomization means via an atomization fuselage at a controlled rate;

an atomization fuselage configured to stabilize the droplet flow by the atomization means;

the at least one ionizer comprises a multi-element ionizer; and the electrostatic collector/precipitator comprises a multi-element electrostatic collector.

In some embodiments of the present disclosure, a particle generating apparatus for producing a plurality of particles of a predetermined size distribution is provided. The apparatus includes a solution container configured to retain a solution including at least one predetermined dissolved substance at a predetermined concentration, at least one pump configured to move the solution from the solution container to the atomization means, and optionally back to the solution container, a scale configured to monitor solution consumption, and atomization means. The atomization means includes an atomizer vessel, and at least one of a pneumatic atomizer and an ultrasonic atomizer configured to atomize the solution to produce a droplet flow comprising a plurality of droplets of the solution. The atomization means also includes at least one air inlet configured to provide air for the droplet flow to at least aid in propelling the plurality of droplets. With respect to the pneumatic atomizer, at least one of a size and/or mass of the droplets and a flowrate thereof can be determined by a configuration of the design of the atomizer, and/or a driving fluid (e.g., air) flow pressure of the atomization nebulizer. With respect to the ultrasonic atomizer, at least one of: a size and/or mass of the droplets and a flowrate thereof, can be determined by at least one of: one or more ultrasonic parameters comprising frequency, amplitude, and/or phase, and design of the atomizer vessel.

In some embodiments, the apparatus further includes a drying chamber, configured to expose the droplet flow to a drying flow so as to produce a dried particle flow having particles of a size and/or mass less than a predetermined threshold size, and direct the dried particle flow with particles of a size lesser than or equal to a predetermined threshold. The drying chamber includes a drying chamber air inlet configured to supply air for the drying flow at a regulated flowrate to regulate at least one of the volume of the droplets and volume of dried particles, a fan configured to provide a constant pressure to the drying flow, a drying chamber outlet, a heater (e.g., a heating element) configured to regulate a temperature profile of the drying flow located at a bottom of the drying chamber, a laminar filter configured to generate a predetermined or preselected homogenous drying flow. The drying chamber is configured to provide a controlled upward directed flow of the drying flow so as to dry the received droplet flow to form the plurality of dried particles, and droplets over a predetermined size and/or mass travel downward against the drying flow for at least one of collection, and disposal.

In some embodiments, the apparatus further includes a connector having a bottom end, a top end, a conduit connecting the first and second ends, and a connector droplet flow outlet, which can be configured as or otherwise comprises an inlet to the drying chamber. The connector is configured such that the first end is arranged downstream from the second end and receives the droplet flow from the atomizer, while returning droplets larger than a predetermined size to the solution container. The threshold size can be determined by the average droplet velocity, which depends on the flow rate and the cross-section area of the connector. The conduit can include at least two turns forming at least one corresponding S-bend (and can be referred to as a staircase connector, according to some embodiments), the second end includes the connector droplet flow outlet (which, in some embodiments corresponds to or otherwise comprises a/the drying chamber inlet) configured to at least one of shape and split the droplet flow into a plurality of flows.

In some embodiments, the apparatus further includes a plurality of ionizers arranged to expose the particle flow received from the drying chamber via the drying chamber outlet, wherein each of the ionizers produce an ionized flow of negative ions configured to charge the particles to produce a charged particle flow.

In some embodiments, the apparatus further includes an electrostatic collector having a predetermined voltage and configured to receive the charged particle flow, includes a central ground electrode protected by a glass tube, an external cylinder having a wall with a surface at the predetermined voltage, and an electrostatic collector exhaust, and is configured to deflect the incoming charged particles of the charged particle flow towards the surface of the wall, such that, the particles form a layer thereon. Additionally, the apparatus further includes a filter configured to capture dried particles from the electrostatic exhaust that are not collected in the electrostatic collector, and an apparatus exhaust arranged to exhaust a remaining flow (the filter, and exhaust may comprise an exhaust assembly for systems, according to at least some embodiments, see., e.g., FIG. 1G).

In some embodiments, the apparatus further includes an electrostatic precipitator, such as any commercially available electrostatic precipitator system (e.g., Kleanland J-series), configured to capture the particles from the particle flow received from the drying chamber via the drying chamber outlet.

Any of the above-noted embodiments (as well as other embodiments disclosed herein), can include at least one of the following additional features, functionality, structure, steps, and/or clarifications (and in some embodiments, a plurality of, and in some embodiments, all of), leading to yet further embodiments of the present disclosure:

- the particle sizes produced by the apparatus is between: 10 and 700 nm, 10 and 600 nm, 10 and 500 nm, 10 and 400 nm, and 10 and 350 nm, 20 and 700 nm, 20 and 600 nm, 20 and 500 nm, 20 and 400 nm, 20 and 350 nm, 30 and 700 nm, 30 and 600 nm, 30 and 500 nm, 30 and 400 nm, 30 and 350 nm, 40 and 700 nm, 40 and 600 nm, 40 and 500 nm, 40 and 400 nm, 40 and 350 nm, 50 and 700 nm, 50 and 600 nm, 50 and 500 nm, 50 and 400 nm, 50 and 350 nm, 60 and 700 nm, 60 and 600 nm, 60 and 500 nm, 60 and 400 nm, 60 and 350 nm, 70 and 700 nm, 70 and 600 nm, 70 and 500 nm, 70 and 400 nm, 70 and 350 nm, 80 and 700 nm, 80 and 600 nm, 80 and 500 nm, 80 and 400 nm, 80 and 350 nm, 90 and 700 nm, 90 and 600 nm, 90 and 500 nm, 90 and 400 nm, 90 and 350 nm, 100 and 700 nm, 100 and 600 nm, 100 and 500 nm, 100 and 400 nm, 100 and 350 nm, 200 and 700 nm, 200 and 600 nm, 200 and 500 nm, 200 and 400 nm, 200 and 350 nm, 300 and 700 nm, 300 and 600 nm, 300 and 500 nm, 300 and 400 nm, 300 and 350 nm, 400 and 700 nm, 400 and 600 nm, 400 and 500 nm, 500 and 700 nm, 500 and 600 nm, 600 and 700 nm, and size ranges between any of the foregoing;
- the at least one substance can be any of a protein, a nucleic acid, a carbohydrate, a small molecule embedded in a protein, an excipient, and a salt;
- the at least one predetermined dissolved substance can be an active pharmaceutical ingredient (API);
- a/the heater, of the drying chamber, can be configured to create a heat gradient inside the drying chamber to a temperature, which can be a predetermined temperature, which in some embodiments, falls in the range of: between 20-80 deg. C., between 30-75 deg. C., between 35-70 deg. C., between 40-65 deg. C., between 45-60 deg. C., between 50-55 deg. C., and below 50 deg. C.; and ranges between any of the foregoing;
- the apparatus, or a portion thereof, can be kept at a constant pressure of between 0.0 to −1.25 mbar (and ranges therebetween), relative to ambient pressure, and in some embodiments, within a range of 0 to −0.3 mbar.
- the ionizer output voltage may be constant or alternating (the ionizer can be a Murata MHM305-01);
- a flowrate through a/the first air inlet of the atomizer can be predetermined and fall within the range of between: 5 and 20 L/min, 6 and 18 L/min, 7 and 16 L/min, 8 and 14 L/min, 9 and 12 L/min, 10 and 11 L/min, 10.5 L/min, 5 and 20 L/min, 5 and 19 L/min, 5 and 18 L/min, 5 and 17 L/min, 5 and 16 L/min, 5 and 15 L/min, 5 and 14 L/min, 5 and 13 L/min, 5 and 12 L/min, 5 and 11 L/min, 5 and 10 L/min, 5 and 9 L/min, 5 and 8 L/min, 5 and 7 L/min, 5 and 6 L/min, 6 and 20 L/min, 6 and 19 L/min, 6 and 18 L/min, 6 and 17 L/min, 6 and 16 L/min, 6 and 15 L/min, 6 and 14 L/min, 6 and 13 L/min, 6 and 12 L/min, 6 and 11 L/min, 6 and 10 L/min, 6 and 9 L/min, 6 and 8 L/min, 6 and 7 L/min, 6 and 6 L/min, 7 and 20 L/min, 7 and 19 L/min, 7 and 18 L/min, 7 and 17 L/min, 7 and 16 L/min, 7 and 15 L/min, 7 and 14 L/min, 7 and 13 L/min, 7 and 12 L/min, 7 and 11 L/min, 7 and 10 L/min, 7 and 9 L/min, 7 and 8 L/min, 8 and 20 L/min, 8 and 19 L/min, 8 and 18 L/min, 8 and 17 L/min, 8 and 16 L/min, 8 and 15 L/min, 8 and 14 L/min, 8 and 13 L/min, 8 and 12 L/min, 8 and 11 L/min, 8 and 10 L/min, 8 and 9 L/min, 9 and 20 L/min, 9 and 19 L/min, 9 and 18 L/min, 9 and 17 L/min, 9 and 16 L/min, 9 and 15 L/min, 9 and 14 L/min, 9 and 13 L/min, 9 and 12 L/min, 9 and 11 L/min, 9 and 10 L/min, 10 and 20 L/min, 10 and 19 L/min, 10 and 18 L/min, 10 and 17 L/min, 10 and 16 L/min, 10 and 15 L/min, 10 and 14 L/min, 10 and 13 L/min, 10 and 12 L/min, 10 and 11 L/min, 11 and 20 L/min, 11 and 19 L/min, 11 and 18 L/min, 11 and 17 L/min, 11 and 16 L/min, 11 and 15 L/min, 11 and 14 L/min, 11 and 13 L/min, 11 and 12 L/min, 12 and 20 L/min, 12 and 19 L/min, 12 and 18 L/min, 12 and 17 L/min, 12 and 16 L/min, 12 and 15 L/min, 12 and 14 L/min, 12 and 13 L/min, 13 and 20 L/min, 13 and 19 L/min, 13 and 18 L/min, 13 and 17 L/min, 13 and 16 L/min, 13 and 15 L/min, 13 and 14 L/min, 14 and 20 L/min, 14 and 19 L/min, 14 and 18 L/min, 14 and 17 L/min, 14 and 16 L/min, 14 and 15 L/min, 15 and 20 L/min, 15 and 19 L/min, 15 and 18 L/min, 15 and 17 L/min, 15 and 16 L/min, 16 and 20 L/min, 16 and 19 L/min, 16 and 18 L/min, 16 and 17 L/min, 17 and 20 L/min, 17 and 19 L/min, 17 and 18 L/min, 18 and 20 L/min, 18 and 19 L/min, 19 and 20 L/min, and ranges between any of the foregoing;
- the predetermined dissolved ingredient concentration can be 1 g/L, and between:
  0.1 to 20 g/L, 0.1 to 19 g/L, 0.1 to 18 g/L, 0.1 to 18 g/L, 0.1 to 19 g/L, 0.1 to 18 g/L, 0.1 to 17 g/L, 0.1 to 16 g/L, 0.1 to 15 g/L, 0.1 to 14 g/L, 0.1 to 13 g/L, 0.1 to 12 g/L, 0.1 to 11 g/L, 0.1 to 10 g/L, 0.1 to 9 g/L, 0.1 to 8 g/L, 0.1 to 7 g/L, 0.1 to 6 g/L, 0.1 to 5 g/L, 0.1 to 4 g/L, 0.1 to 3 g/L, 0.1 to 2 g/L, 0.1 to 1 g/L, 1 to 20 g/L, 1 to 19 g/L, 1 to 18 g/L, 1 to 17 g/L, 1 to 16 g/L, 1 to 15 g/L, 1 to 14 g/L, 1 to 13 g/L, 1 to 12 g/L, 1 to 11 g/L, 1 to 10 g/L, 1 to 9 g/L, 1 to 8 g/L, 1 to 7 g/L, 1 to 6 g/L, 1 to 5 g/L, 1 to 4 g/L, 1 to 3 g/L, 1 to 2 g/L, 2 to 20 g/L, 2 to 19 g/L, 2 to 18 g/L, 2 to 17 g/L, 2 to 16 g/L, 2 to 15 g/L, 2 to 14 g/L, 2 to 13 g/L, 2 to 12 g/L, 2 to 11 g/L, 2 to 10 g/L, 2 to 9 g/L, 2 to 8 g/L, 2 to 7 g/L, 2 to 6 g/L, 2 to 5 g/L, 2 to 4 g/L, 2 to 3 g/L, 3 to 20 g/L, 3 to 19 g/L, 3 to 18 g/L, 3 to 17 g/L, 3 to 16 g/L, 3 to 15 g/L, 3 to 14 g/L, 3 to 13 g/L, 3 to 12 g/L, 3 to 11 g/L, 3 to 10 g/L, 3 to 9 g/L, 3 to 8 g/L, 3 to 7 g/L, 3 to 6 g/L, 3 to 5 g/L, 3 to 4 g/L, 4 to 20 g/L, 4 to 19 g/L, 4 to 18 g/L, 4 to 17 g/L, 4 to 16 g/L, 4 to 15 g/L, 4 to 14 g/L, 4 to 13 g/L, 4 to 12 g/L, 4 to 11 g/L, 4 to 10 g/L, 4 to 9 g/L, 4 to 8 g/L, 4 to 7 g/L, 4 to 6 g/L, 4 to 5 g/L, 5 to 20 g/L, 5 to 19 g/L, 5 to 18 g/L, 5 to 17 g/L, 5 to 16 g/L, 5 to 15 g/L, 5 to 14 g/L, 5 to 13 g/L, 5 to 12 g/L, 5 to 11 g/L, 5 to 10 g/L, 5 to 9 g/L, 5 to 8 g/L, 5 to 7 g/L, 5 to 6 g/L, 6 to 20 g/L, 6 to 19 g/L, 6 to 18 g/L, 6 to 17 g/L, 6 to 16 g/L, 6 to 15 g/L, 6 to 14 g/L, 6 to 13 g/L, 6 to 12 g/L, 6 to 11 g/L, 6 to 10 g/L, 6 to 9 g/L, 6 to 8 g/L, 6 to 7 g/L, 7 to 20 g/L, 7 to 19 g/L, 7 to 18 g/L, 7 to 17 g/L, 7 to 16 g/L, 7 to 15 g/L, 7 to 14 g/L, 7 to 13 g/L, 7 to 12 g/L, 7 to 11 g/L, 7 to 10 g/L, 7 to 9 g/L, 7 to 8 g/L, 8 to 20 g/L, 8 to 19 g/L, 8 to 18 g/L, 8 to 17 g/L, 8 to 16 g/L, 8 to 15 g/L, 8 to 14 g/L, 8 to 13 g/L, 8 to 12 g/L, 8 to 11 g/L, 8 to 10 g/L, 8 to 9 g/L, 9 to 20 g/L, 9 to 19 g/L, 9 to 18 g/L, 9 to 17 g/L, 9 to 16 g/L, 9 to 15 g/L, 9 to 14 g/L, 9 to 13 g/L, 9 to 12 g/L, 9 to 11 g/L, 9 to 10 g/L, 10 to 20 g/L, 10 to 19 g/L, 10 to 18 g/L, 10 to 17 g/L, 10 to 16 g/L, 10 to 15 g/L, 10 to 14 g/L, 10 to 13 g/L, 10 to 12 g/L, 10 to 11 g/L, 11 to 20 g/L, 11 to 19 g/L, 11 to 18 g/L, 11 to 17 g/L, 11 to 16 g/L, 11 to 15 g/L, 11 to 14 g/L, 11 to 13 g/L, 11 to 12 g/L, 12 to 20 g/L, 12 to 19 g/L, 12 to 18 g/L, 12 to 17 g/L, 12 to 16 g/L, 12 to 15 g/L, 12 to 14 g/L, 12 to 13 g/L, 13 to 20 g/L, 13 to 19 g/L, 13 to 18 g/L, 13 to 17 g/L, 13 to 16 g/L, 13 to 15 g/L, 13 to 14 g/L, 14 to 20 g/L, 14 to 19 g/L, 14 to 18 g/L, 14 to 17 g/L, 14 to 16 g/L, 14 to 15 g/L, 15 to 20 g/L, 15 to 19 g/L, 15 to 18 g/L, 15 to 17 g/L, 15 to 16 g/L, 16 to 20 g/L, 16 to 19 g/L, 16 to 18 g/L, 16 to 17 g/L, 17 to 20 g/L, 17 to 19 g/L, 17 to 18 g/L, 18 to 20 g/L, 18 to 19 g/L, 19 to 20 g/L, and ranges between any of the forgoing;

and a flowrate, which can be predetermined, of a/the drying flow can fall within the range of between:

50 and 200 L/min, 60 and 200 L/min, 70 and 200 L/min, 80 and 200 L/min, 90 and 200 L/min, 100 and 200 L/min, 110 and 200 L/min, 120 and 200 L/min, 130 and 200 L/min, 140 and 200 L/min, 150 and 200 L/min, 160 and 200 L/min, 170 and 200 L/min, 180 and 200 L/min, 190 and 200 L/min, 50 and 60 L/min, 50 and 70 L/min, 50 and 80 L/min, 50 and 90 L/min, 50 and 100 L/min, 50 and 110 L/min, 50 and 120 L/min, 50 and 130 L/min, 50 and 140 L/min, 50 and 150 L/min, 50 and 160 L/min, 50 and 170 L/min, 50 and 180 L/min, 50 and 190 L/min, 50 and 200 L/min, 60 and 70 L/min, 60 and 80 L/min, 60 and 90 L/min, 60 and 100 L/min, 60 and 110 L/min, 60 and 120 L/min, 60 and 130 L/min, 60 and 140 L/min, 60 and 150 L/min, 60 and 160 L/min, 60 and 170 L/min, 60 and 180 L/min, 60 and 190 L/min, 60 and 200 L/min, 70 and 80 L/min, 70 and 90 L/min, 70 and 100 L/min, 70 and 110 L/min, 70 and 120 L/min, 70 and 130 L/min, 70 and 140 L/min, 70 and 150 L/min, 70 and 160 L/min, 70 and 170 L/min, 70 and 180 L/min, 70 and 190 L/min, 70 and 200 L/min, 80 and 90 L/min, 80 and 100 L/min, 80 and 110 L/min, 80 and 120 L/min, 80 and 130 L/min, 80 and 140 L/min, 80 and 150 L/min, 80 and 160 L/min, 80 and 170 L/min, 80 and 180 L/min, 80 and 190 L/min, 80 and 200 L/min, 90 and 100 L/min, 90 and 110 L/min, 90 and 120 L/min, 90 and 130 L/min, 90 and 140 L/min, 90 and 150 L/min, 90 and 160 L/min, 90 and 170 L/min, 90 and 180 L/min, 90 and 190 L/min, 90 and 200 L/min, 100 and 110 L/min, 100 and 120 L/min, 100 and 130 L/min, 100 and 140 L/min, 100 and 150 L/min, 100 and 160 L/min, 100 and 170 L/min, 100 and 180 L/min, 100 and 190 L/min, 100 and 200 L/min, 110 and 120 L/min, 110 and 130 L/min, 110 and 140 L/min, 110 and 150 L/min, 110 and 160 L/min, 110 and 170 L/min, 110 and 180 L/min, 110 and 190 L/min, 110 and 200 L/min, 120 and 130 L/min, 120 and 140 L/min, 120 and 150 L/min, 120 and 160 L/min, 120 and 170 L/min, 120 and 180 L/min, 120 and 190 L/min, 120 and 200 L/min, 130 and 140 L/min, 130 and 150 L/min, 130 and 160 L/min, 130 and 170 L/min, 130 and 180 L/min, 130 and 190 L/min, 130 and 200 L/min, 140 and 150 L/min, 140 and 160 L/min, 140 and 170 L/min, 140 and 180 L/min, 140 and 190 L/min, 140 and 200 L/min, 150 and 160 L/min, 150 and 170 L/min, 150 and 180 L/min, 150 and 190 L/min, 150 and 200 L/min, 160 and 170 L/min, 160 and 180 L/min, 160 and 190 L/min, 160 and 200 L/min, 170 and 180 L/min, 170 and 190 L/min, 170 and 200 L/min, 180 and 190 L/min, 180 and 200 L/min, 190 and 200 L/min, and ranges between any of the foregoing.

In some embodiments, a drying chamber device for a particle generating apparatus is provided and is configured to expose a droplet flow to a drying flow so as to produce a dried particle flow having particles of a size and/or mass less than a predetermined threshold size. In such embodiments (as well as other embodiments disclosed herein), the following additional features, functionality, structure, steps, and/or clarifications (and in some embodiments, a plurality of, and in some embodiments, all of) can be included, leading to yet further embodiments of the present disclosure:

a drying chamber air inlet configured to supply air for the drying flow at a regulated flowrate to regulate at least one of the volume of the droplets and volume of dried particles;

at least one of a fan/pump configured to provide a constant pressure to the drying flow, a drying chamber outlet, a heater configured to regulate a temperature of the drying flow located at a bottom of the drying chamber, and a laminar filter configured to homogenize the drying flow;

and the drying chamber can be configured to provide a controlled upward directed flow of the drying flow so as to dry the received droplet flow to form the plurality of dried particles, and/or droplets over a predetermined size and/or mass travel downward against the drying flow for at least one of collection, and disposal.

In some embodiments, a connector device for a particle generating apparatus is provided and includes a bottom end, a top end, a conduit connecting the first and second ends, and a connector droplet flow inlet to the drying chamber. In such embodiments, the device can be configured such that the first end is arranged downstream from the second end and receives the droplet flow from the atomizer, while returning droplets larger than a predetermined size to the solution container. The conduit can include at least two turns forming at least one corresponding S-bend (for example), and/or the second end includes the connector air outlet (which in some embodiments, corresponds to or otherwise comprises a/the drying chamber inlet) configured to at least one of shape and split the droplet flow into a plurality of flows.

In some embodiments, an electrostatic collector device for a particle generating apparatus is provided and includes a central ground electrode protected by a glass/ceramic tube, an external cylinder having a wall with a surface at the predetermined voltage. In such embodiments, the device is arranged with a particle generating device so as to expose a particle flow to an ionized flow of negative ions configured to charge particles in the particle flow to produce a charged particle flow.

Any of the above-noted embodiments (as well as other embodiments disclosed herein), can include at least one of the following additional features, functionality, structure, steps, and/or clarifications (and in some embodiments, a plurality of, and in some embodiments, all of), leading to yet further embodiments of the present disclosure:

- an electrostatic collector exhaust;
- the device is configured to receive a charged particle flow; and
- the device is configured to deflect incoming charged particles, deflect incoming charged particles towards a surface, where, in some embodiments, the particles are deflected toward the surface to form a layer thereon (e.g., a layer on a wall).

In some embodiments, a method of producing a population of particles is provided and includes atomizing a solution featuring a dissolved molecule of a predetermined concentration to produce a plurality of droplets in a droplet flow, separating the droplets of less than or equal to a threshold size and/or mass in the droplet flow using gravity and upward flow along a connector (and/or among turns of the connector), where droplets greater than the threshold size and/or mass flow back against the upward flow and are collected or discarded, and directing or otherwise exposing the droplet flow containing the droplets of less than the threshold size into one or more drying flows, where the drying flows provide a controlled upward directed flow of elevated temperature air or gas so as to evaporate the droplets to produce a plurality of dried particles in a dried particle flow. The particles and/or droplets having a size and/or mass greater than a threshold amount too heavy to be retained in the upward drying airflows, fall down and be discarded. Charging the dried particles in the dried particle flow with a flow of negative ions establishing a charged particle flow, and deflecting the charged particle flow via an electrostatic collection device onto a surface for collection thereof.

In some embodiments, a population of particles produced by at least some of the apparatus, system, and/or device embodiments disclosed herein, having a size of: 10 and 700 nm, 20 and 600 nm, 30 and 500 nm, 40 and 400 nm, and 50 and 350 nm, and size ranges between any of the foregoing.

In some embodiments, a population of particles produced by at least some of the apparatus, system, device, and method embodiments disclosed herein, having a size distribution of D50 (corresponding to 160 nm).

In some embodiments, a method for producing a population of particle is provided and includes at least one of a pneumatic atomizer and an ultrasonic atomizer.

Various embodiments, and elements/features/functionality thereof, can be scaled (e.g., enlarged) for production of a desired amount of particles, from laboratory to industrial scales. Accordingly, various flowrates, material amounts, and the like may also be scaled to obtain specific production requirements.

These and other embodiments, objects and advantages will become even more evident with reference to the concurrently filed figures, a brief description of which is set out below, and following detailed description of at least some of the embodiments.

BRIEF DESCRIPTION OF THE FIGURES

FIG. 1D-2 illustrates an assembled perspective and partially transparent view, with hidden lines, of at least a portion of a particle generating apparatus according to some embodiments of the disclosure.

FIG. 1D-3 illustrates a side view of a straight connector for connecting atomizer means (e.g., via an atomization fuselage) to a drying chamber of a particle generating apparatus, according to some embodiments of the disclosure.

FIG. 2 is a graph of ionizer voltage versus supply voltage for an ionizer for a particle generating apparatus according to some embodiments of the disclosure.

DETAILED DESCRIPTION

Figure 3A:
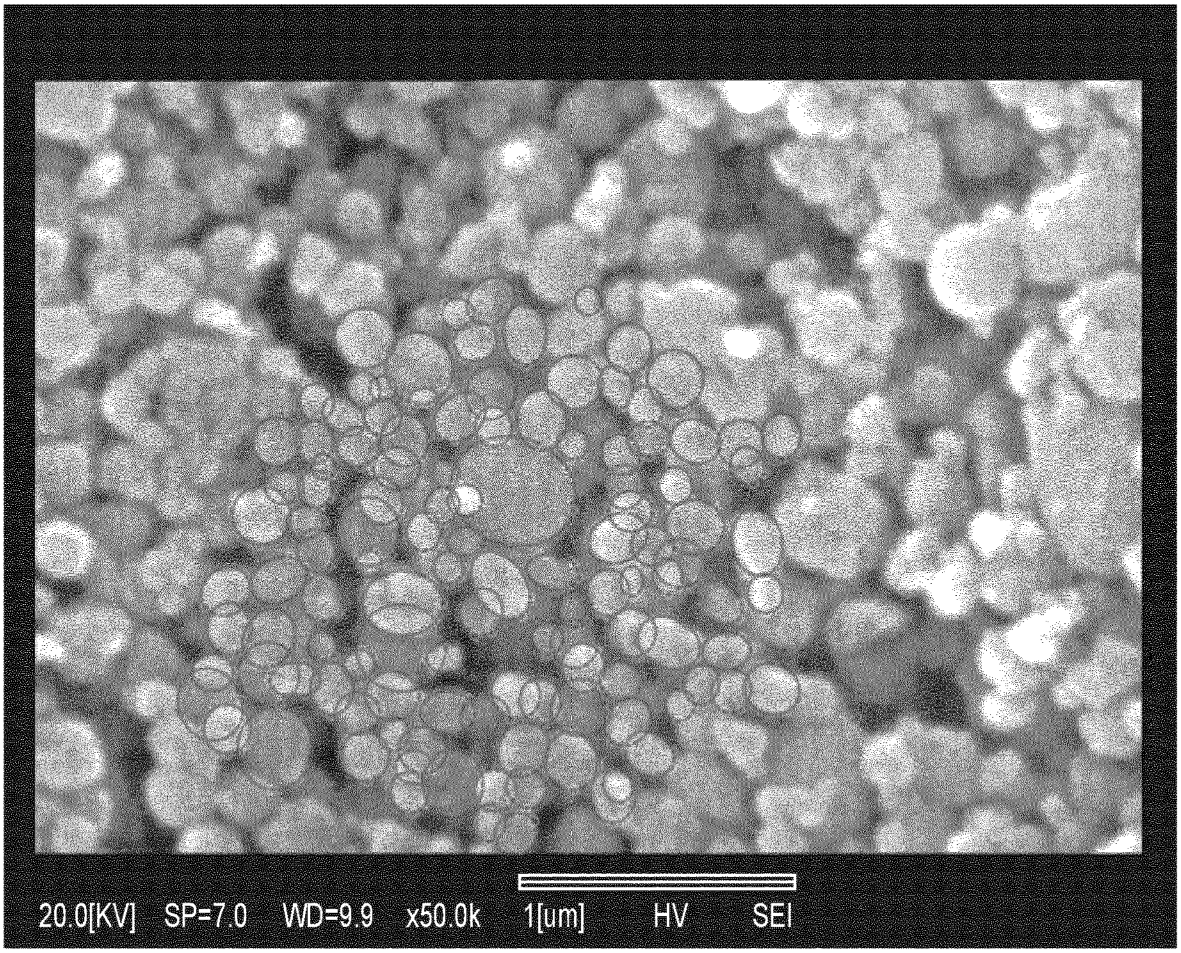
FIG. 3A is an SEM image of particles generated by a particle generating apparatus according to some embodiments of the disclosure.
Figure 3B:
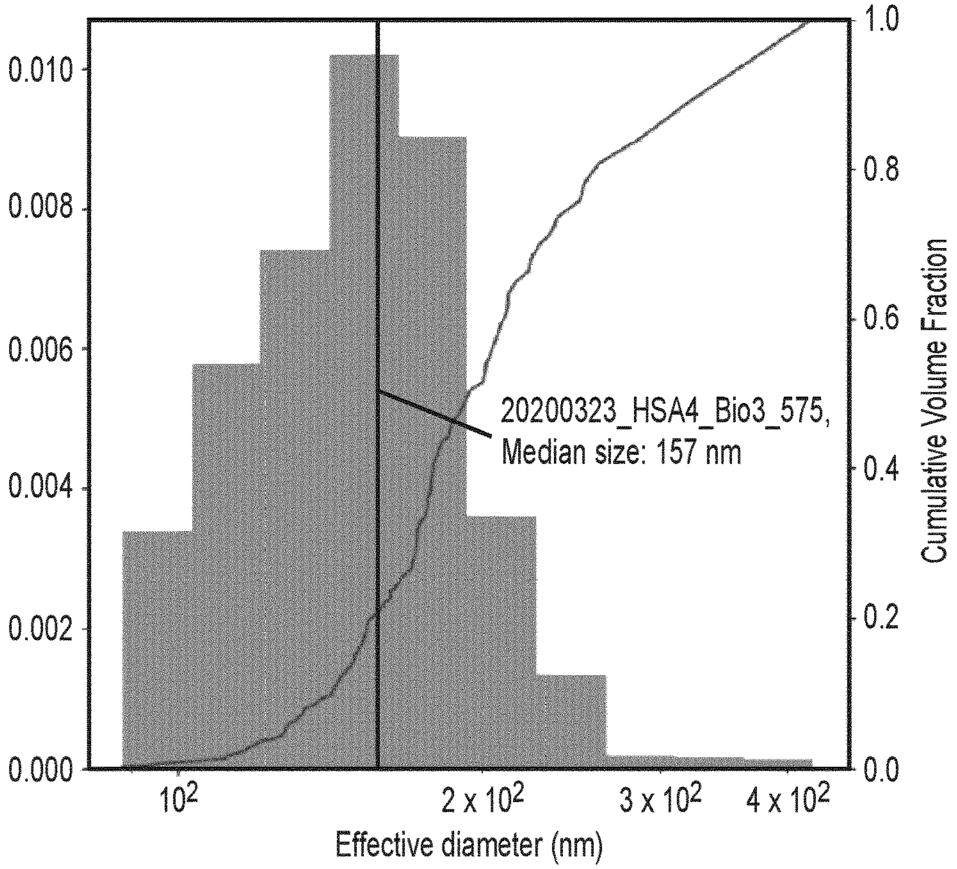
FIG. 3B is a number histogram illustrating effective diameter of particles (shown in FIG. 3A) vs. cumulative volume fraction generated by a particle generating apparatus according to some embodiments of the disclosure.
Figure 3C:
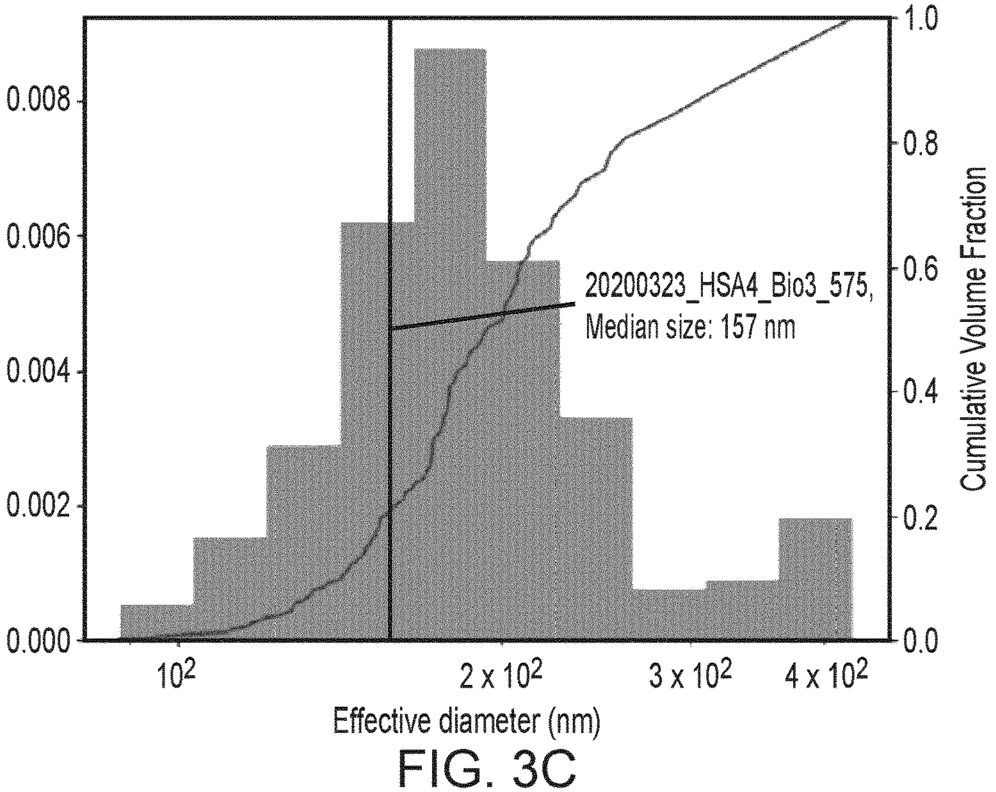
FIG. 3C is a volume histogram illustrating effective diameter of particles (shown in FIG. 3A) vs. cumulative volume fraction generated by a particle generating apparatus according to some embodiments of the disclosure.

An example of the systems, apparatuses, and devices, according to various embodiments of the present disclosure are illustrated in FIGS. 1A-1K. Accordingly, the disclosed embodiments correspond to an apparatus (which may also be referred to as a system, apparatus and system used interchangeably throughout) for producing a population of particles sized, in some embodiments, between, depending upon the embodiments: 10 and 700 nm, 20 and 600 nm, 30 and 500 nm, 40 and 400 nm, and 50 and 350 nm, and in some embodiments, size ranges therebetween. FIG. 3A is an SEM image of particles generated by a particle generating apparatus according to some embodiments of the disclosure. Correspondingly, FIG. 3B is a number histogram graph illustrating effective diameter of particles shown in FIG. 3A generated by a particle generating apparatus according to some embodiments of the disclosure, and FIG. 3C is a volume histogram graph of the particles shown in FIG. 3A and generated by a particle generating apparatus according to some embodiments of the disclosure.

As shown in the figures, in some embodiments, an apparatus 1000 includes a solution container (not shown) configured to retain a solution including at least one predetermined dissolved substance at a predetermined concentration (which can be delivered to the atomizer via a solution inlet 1310 (excess solution can exit via a solution outlet 1312). In some embodiments, the apparatus includes at least one pump (e.g., Boxer GmbH 9QX peristaltic pump) configured to move the solution from the solution container to an atomization means (not shown), and optionally to the solution container, a scale (not shown) (e.g., Ohaus Scout SKX1202) may be provided and configured to monitor solution consumption. The solution container stands on a scale outside the fuselage. The container is connected to the nebulizer with tubes which bring the solution into the nebulizer inside the fuselage. The tubes pass via a pump which is located outside the fuselage. The pump is located between the container and the fuselage.

As shown in FIGS. 1H-1O, the atomization means (which in some embodiments, comprises an Omron NEB-NSET3-81E), in some embodiments, includes an atomizer fuselage 1300 including at least one of a pneumatic atomizer and an ultrasonic atomizer (both referred to as ref. no. 1302) configured to atomize the solution to produce a droplet flow comprising a plurality of droplets of the solution. The fuselage 1300 includes an ambient air/gas inlet 1304, a pressurized air/gas inlet 1306, a mist outlet 1308, a solution inlet 1310, and a solution outlet 1312. The fuselage can be a housing, which can include transparent side portions for viewing the atomization means (nebulizer), with fixation means (e.g., fasteners) for keeping the fuselage housing contained. It is noted, with reference to FIGS. 1M and 1O, that the atomizer 1302 is illustrated in cross-sectional/hatched form for illustrative convenience only and is not intended to illustrate the inner mechanisms and details of a nebulizer/atomizer.

The atomization means (see 1302 in FIGS. 1M-1O) also includes a first air inlet located at a bottom portion 1010 of the apparatus configured to provide air for the droplet flow to at least aid in propelling the plurality of droplets. With respect to the pneumatic atomizer, at least one of a size and/or mass of the droplets and a flowrate thereof can be determined by a configuration of an atomization nozzle (e.g., Omron NEB-NSET3-81E or similar), and/or a driving airflow pressure (in some embodiments, between 4.8 to 6.0 bar, and ranges therebetween) of the atomization nozzle. With respect to the ultrasonic atomizer, at least one of: a size and/or mass of the droplets and a flowrate thereof, can be determined by at least one of: one or more ultrasonic parameters comprising frequency, amplitude, and/or phase, and design of the atomizer vessel (e.g., Omron NEB-NSET3-81E or similar).

Figure 4A:
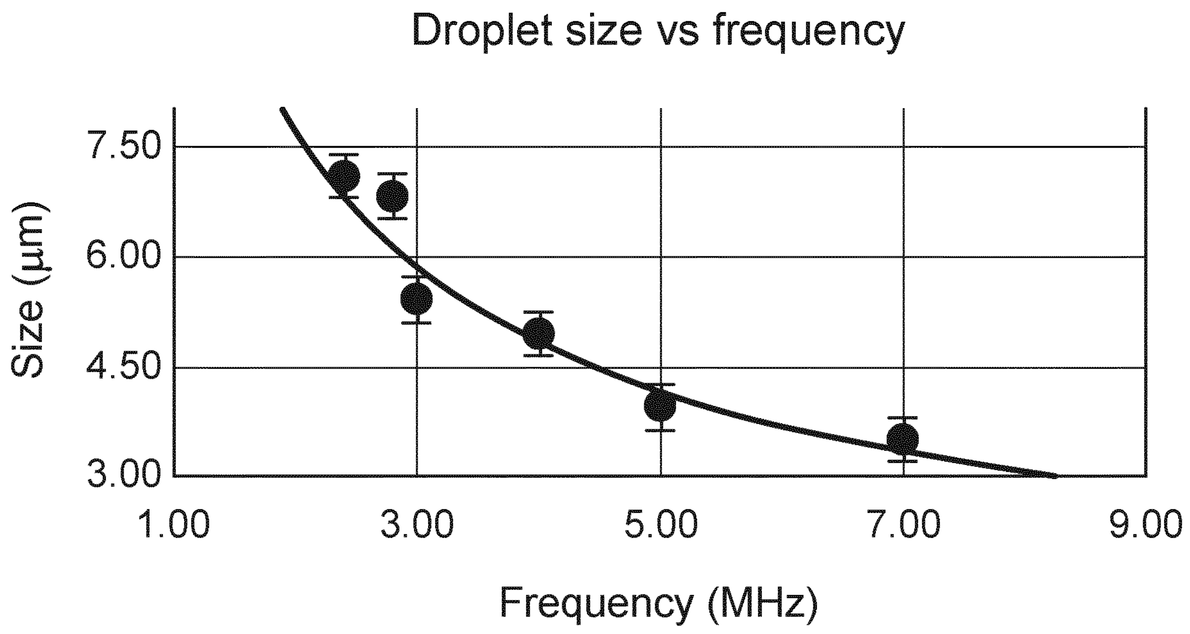
FIG. 4A is a chart illustrating droplet sizes at different frequencies, produced by an ultrasonic atomizer for a particle generating apparatus according to some embodiments of the disclosure.
Figure 4B:
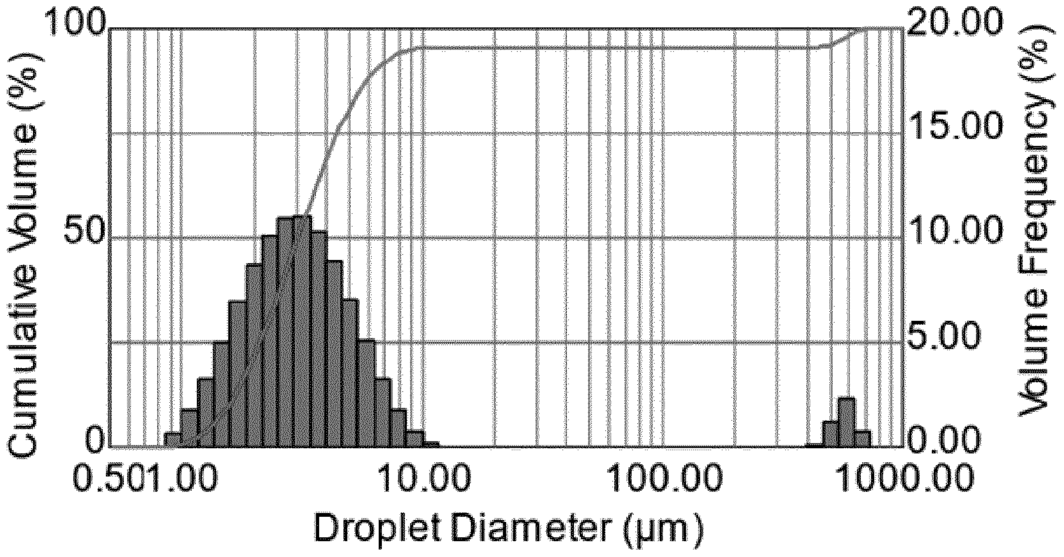
FIG. 4B is a chart illustrating nominal droplet size from a two-fluid nozzle, for a particle generating apparatus according to some embodiments of the disclosure.
Figure 5A:
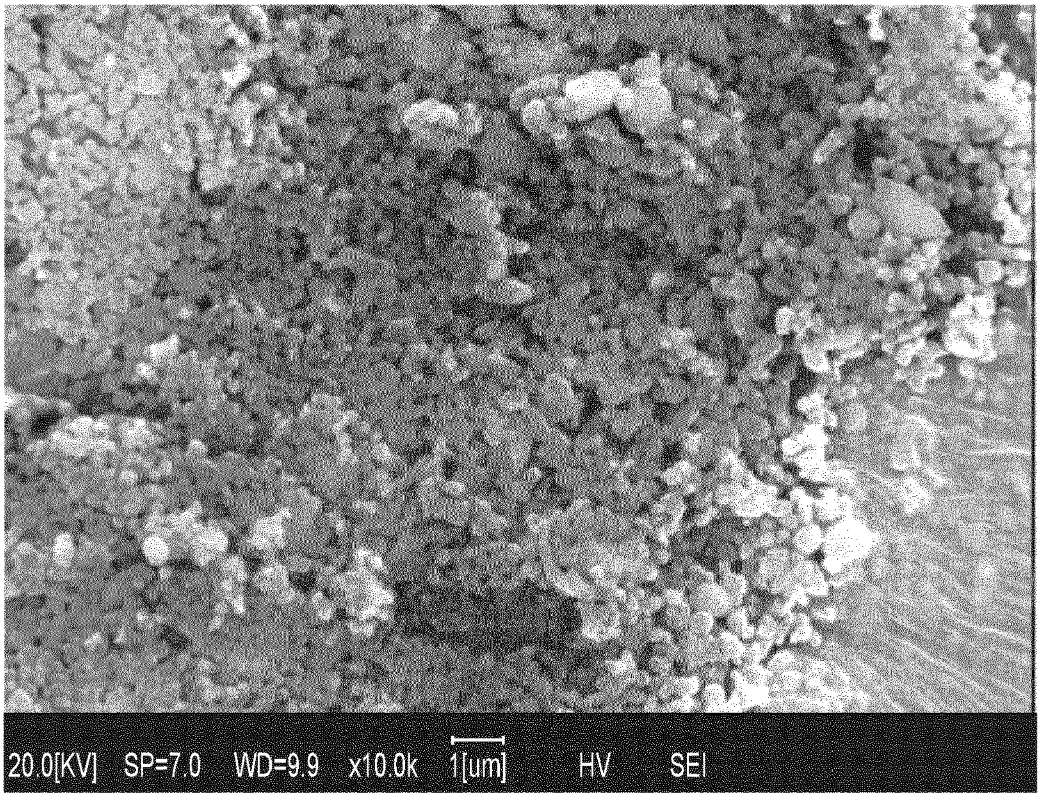
FIG. 5A is an image of particles formed from an ultrasonic atomizer for a particle generating apparatus according to some embodiments of the present disclosure.
Figure 5B:
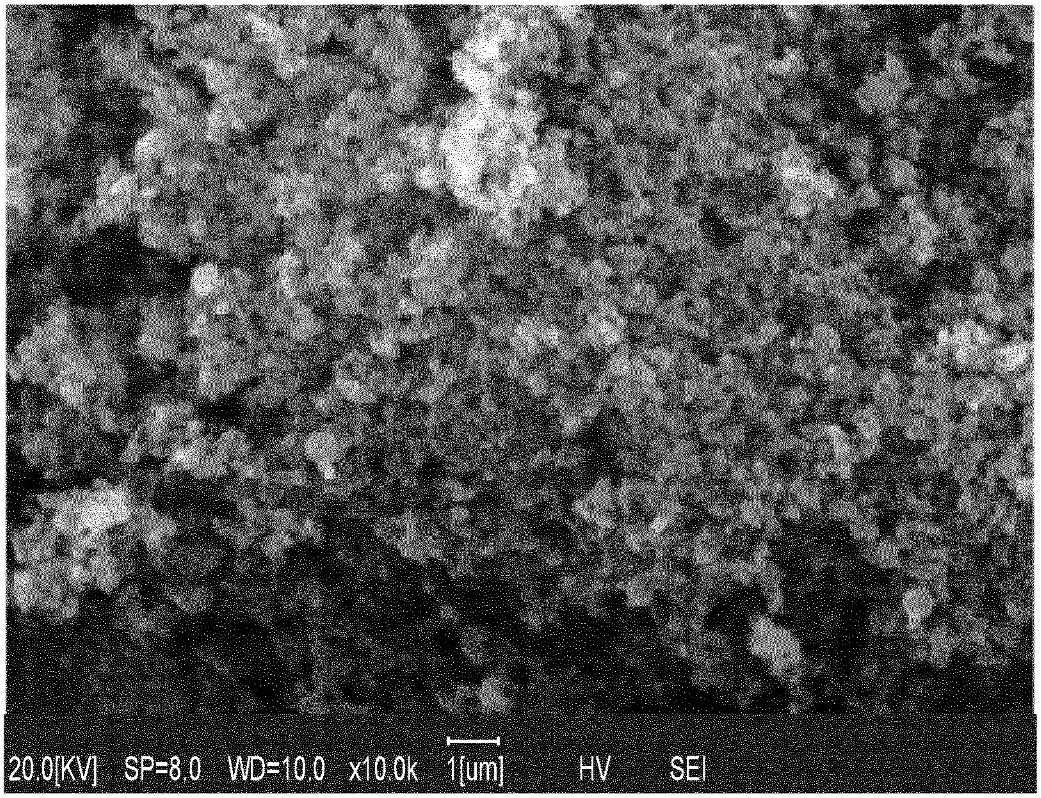
FIG. 5B is an image of particles formed by a two-fluid nozzle of an atomizer for a particle generating apparatus according to some embodiments of the present disclosure.
Figure 5C:
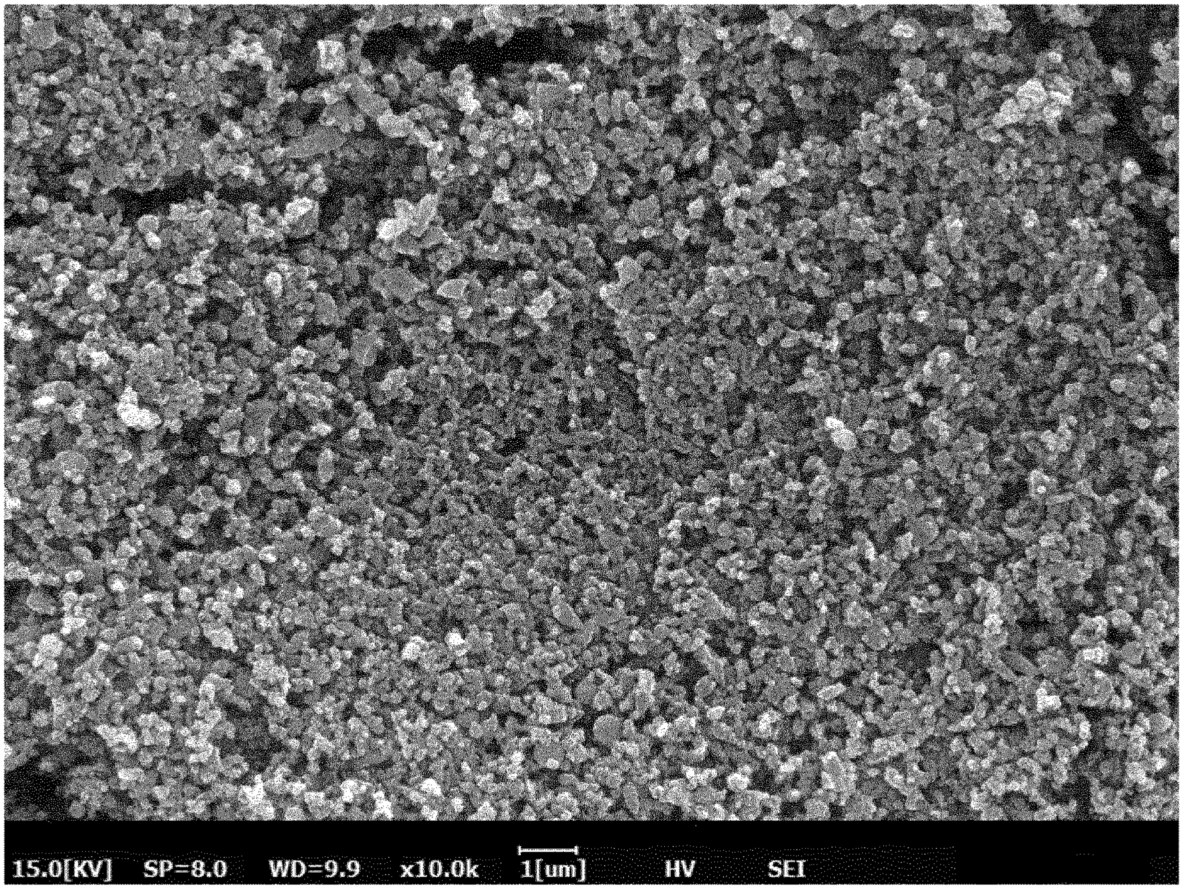
FIG. 5C is an image of insulin particles formed by a two-fluid nozzle of an atomizer for a particle generating apparatus according to some embodiments of the present disclosure.

In some embodiments, the atomizer can comprise an ultrasonic atomizer having a piezoelectric crystal/ceramic/actuator that focuses ultrasonic acoustic energy to a point. Accordingly, fluid exposed to the acoustic energy breaks up into small droplets that are carried upstream by a/the drying airflow in a/the drying chamber (see below and throughout). In some embodiments, the droplet size decreases as the ultrasonic frequency increases. In some embodiments, an ultrasonic frequency range of between 2.4 to 7 MHz can be used. FIG. 4A, is a graph illustrating measured droplet sizes at different frequencies (dots) compared to the theoretical prediction (blue), with the smallest droplet size being 3.5 micrometers. FIG. 4B, is a graph illustrating measured nominal droplet size from a two-fluid nozzle, where the DV50 value is 3.0 micrometers (blue bars on the right-hand side are artifacts originated by dust on the optics. Correspondingly, FIG. 5A is an image of particles formed from an ultrasonic atomizer for a particle generating apparatus according to some embodiments of the present disclosure, FIG. 5B is an image of particles formed by a two fluid nozzle of an atomizer for a particle generating apparatus according to some embodiments of the present disclosure, and FIG. 5C is an image of insulin particles formed by a two-fluid nozzle for a particle generating apparatus according to some embodiments of the present disclosure.

In some embodiments, another type of ultrasonic atomizer that can be is a mesh atomizer, which comprises a perforated metal (e.g., steel) sheet sandwiched between two piezoelectric rings. Here, droplet size depends on a size of the holes within the metal sheet, which, in some embodiments, may be periodically arranged in a lattice featuring from 1 to 10000 elements, and which may be, according to some embodiments, separated by a distance of 50 to 450 micrometers with a pore diameter, in some embodiments of between 2 and 12 micrometers. Additionally, an operating frequency, in some embodiments, corresponds to frequencies ranging from 95 to 190 kHz.

In some embodiments, operational voltage range (ultrasonic signal amplitude) for ultrasonic atomizers depends on the nature of the piezoelectric material as well as the material thickness, but can vary between 30 to 70 V.

Figure 1A:
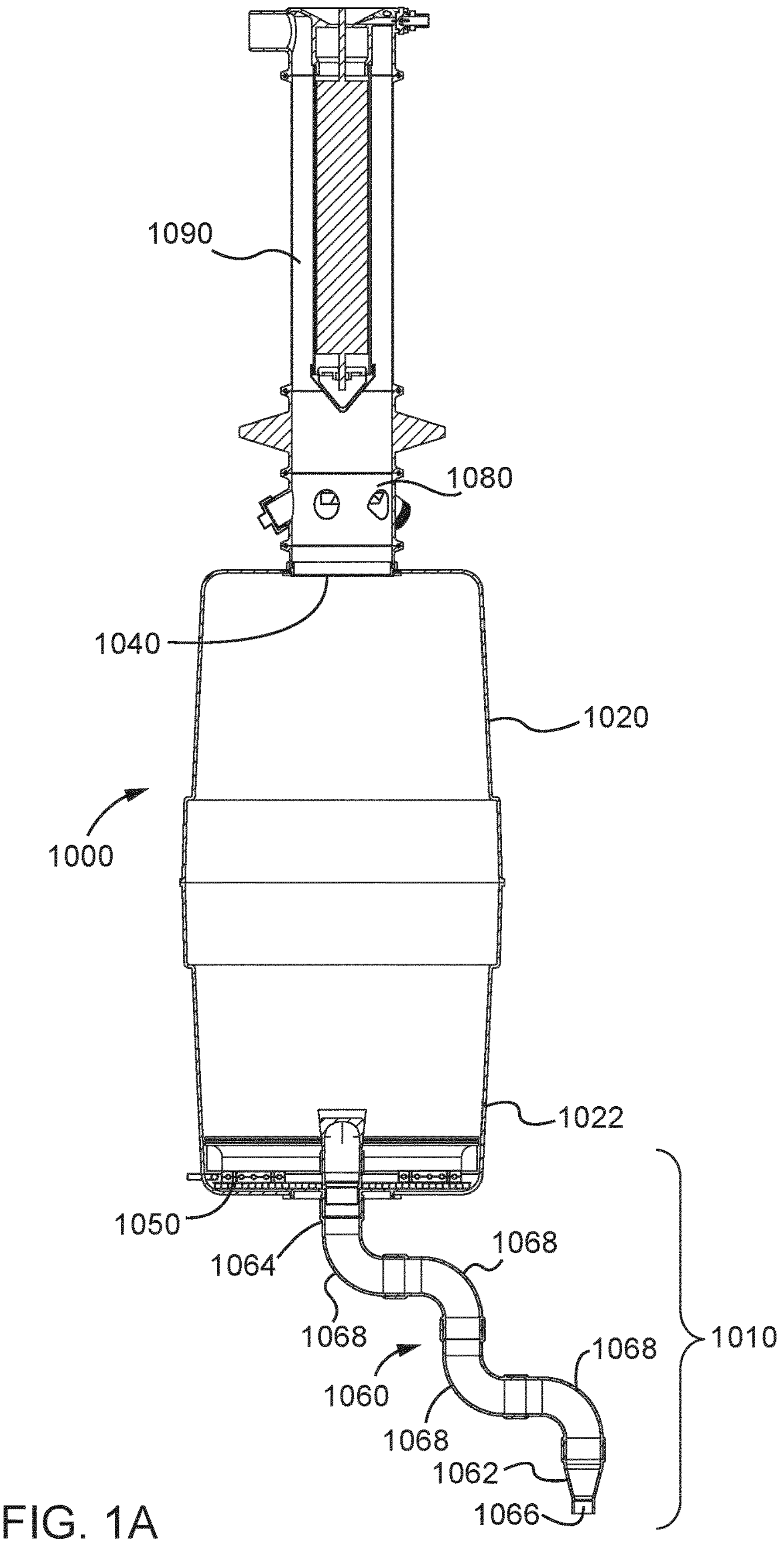
FIG. 1A illustrates an assembled, cross-sectional first side view of at least a portion of a particle generating apparatus according to some embodiments of the disclosure.
Figure 1B:
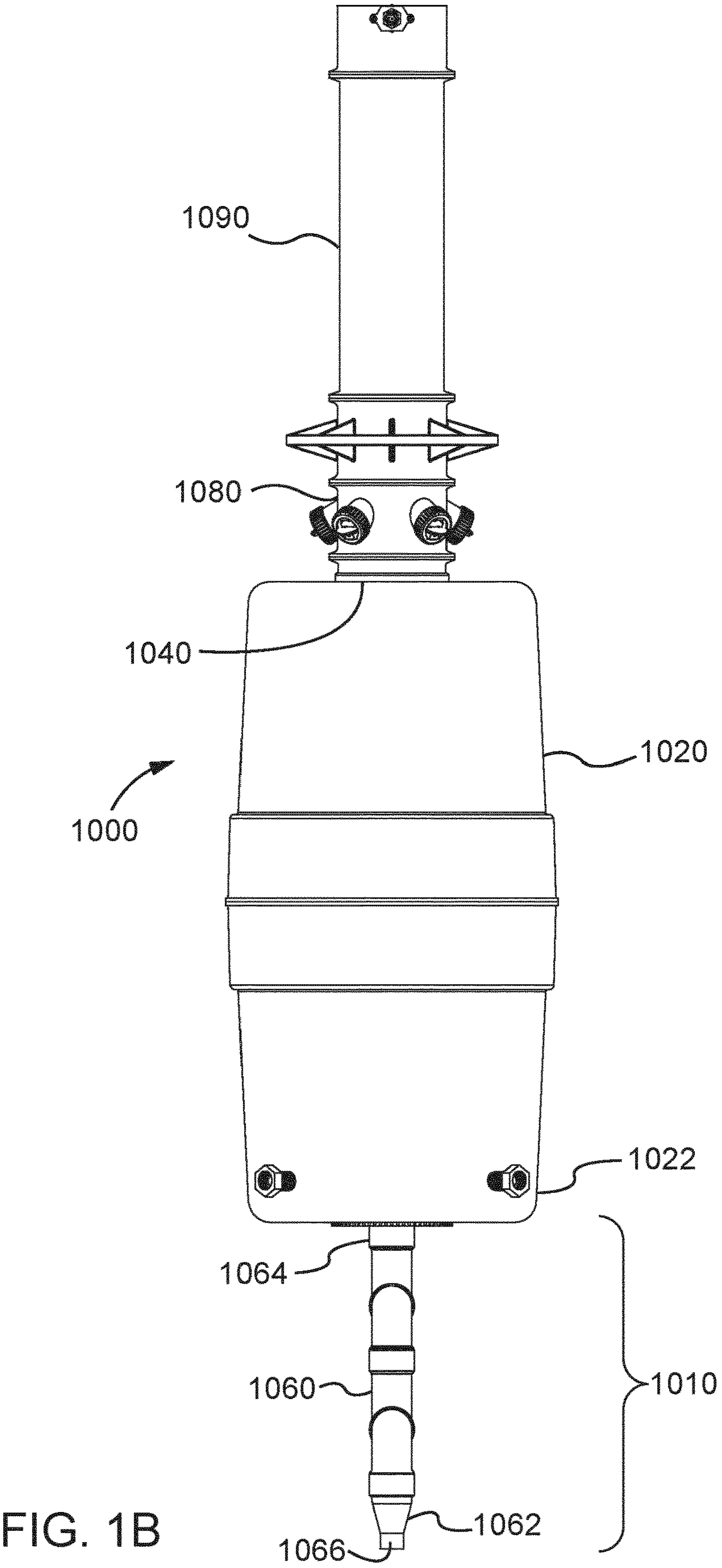
FIG. 1B illustrates an assembled second side view of at least a portion of a particle generating apparatus according to some embodiments of the disclosure.
Figure 1C:
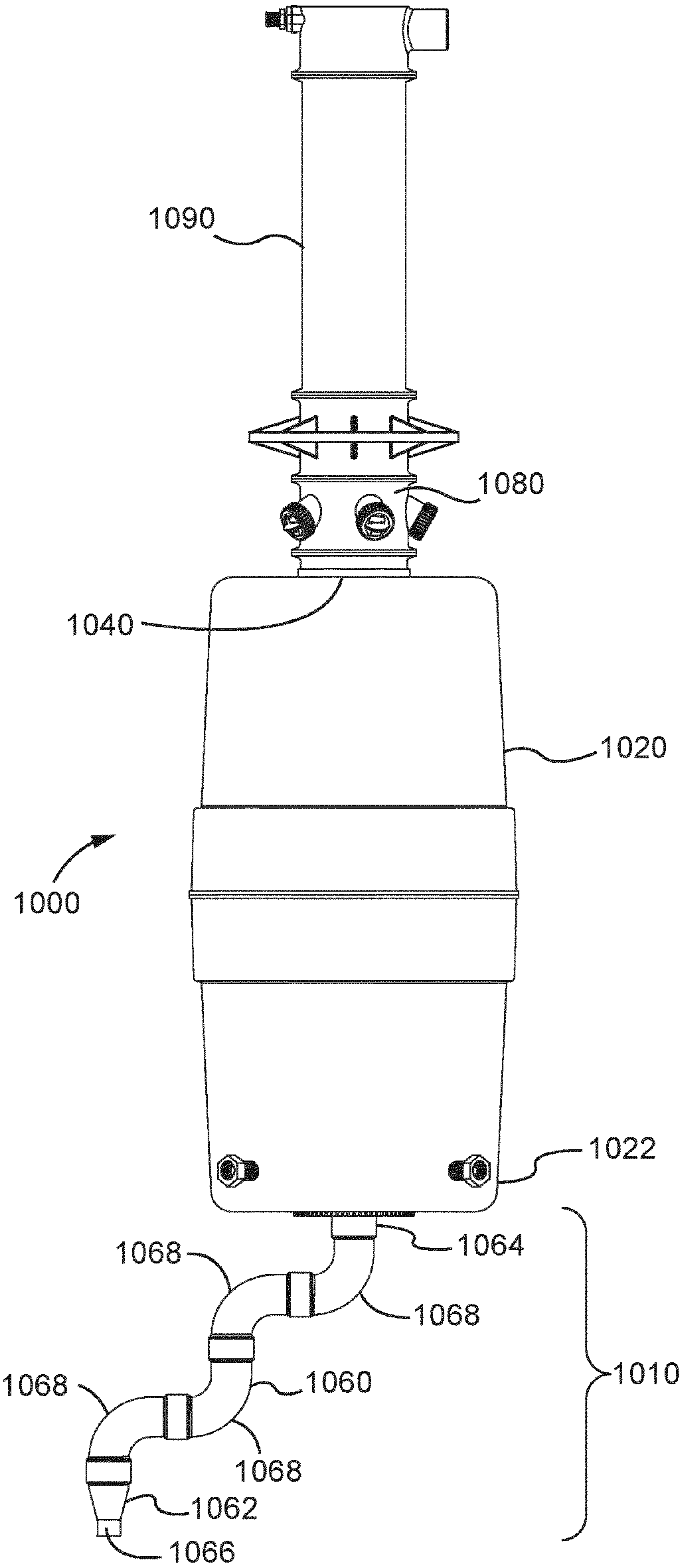
FIG. 1C illustrates an assembled third side view of at least a portion of a particle generating apparatus according to some embodiments of the disclosure.
Figures 1, 1D:
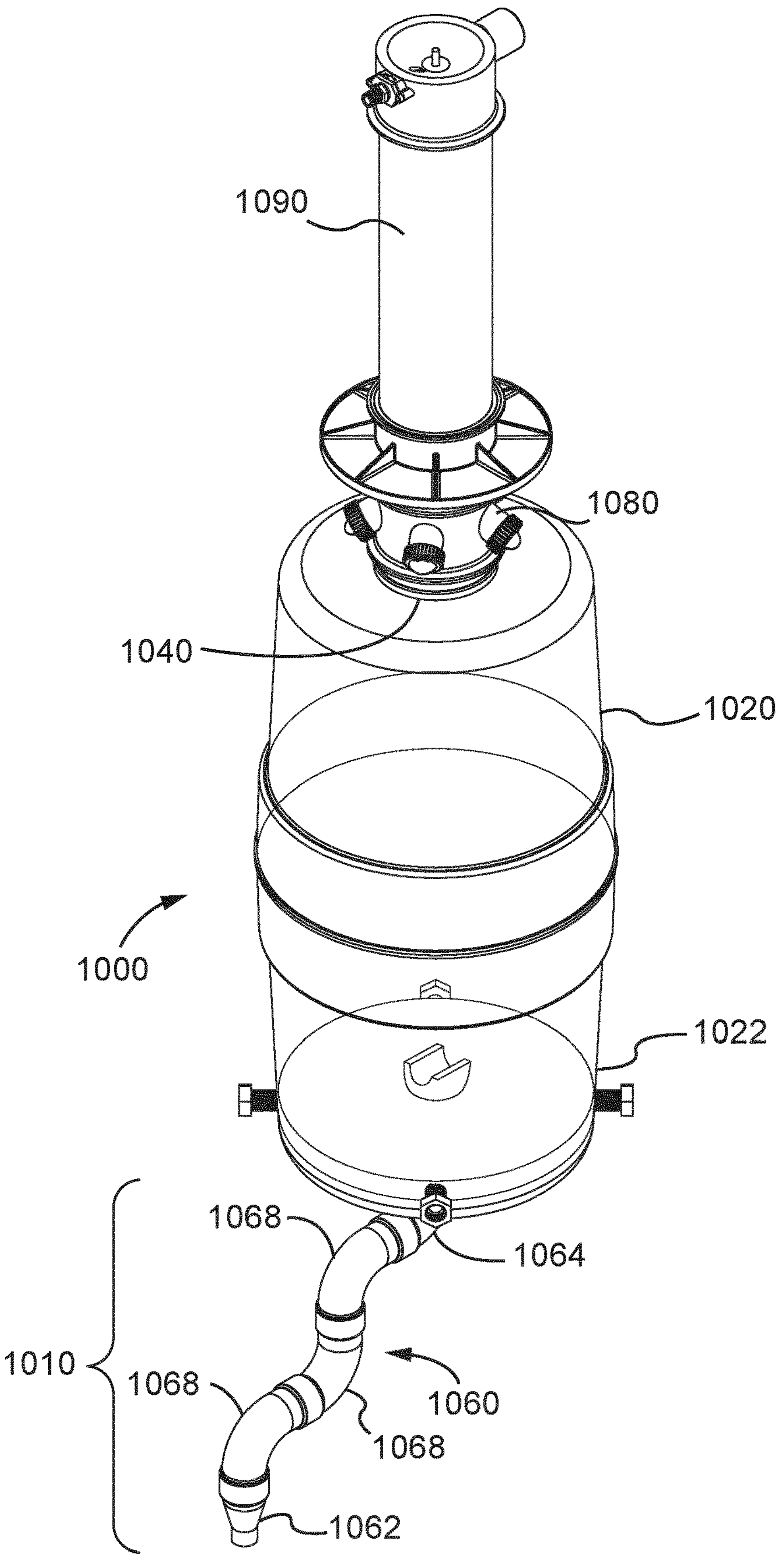
FIG. 1D-1 illustrates an assembled perspective and partially transparent view of at least a portion of a particle generating apparatus according to some embodiments of the disclosure.
Figures 1, 1D, 2, 3:
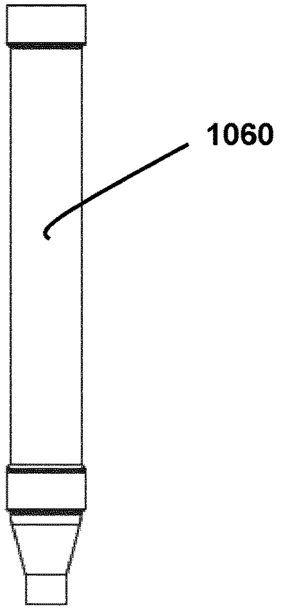
Figures 1, 1D, 2:
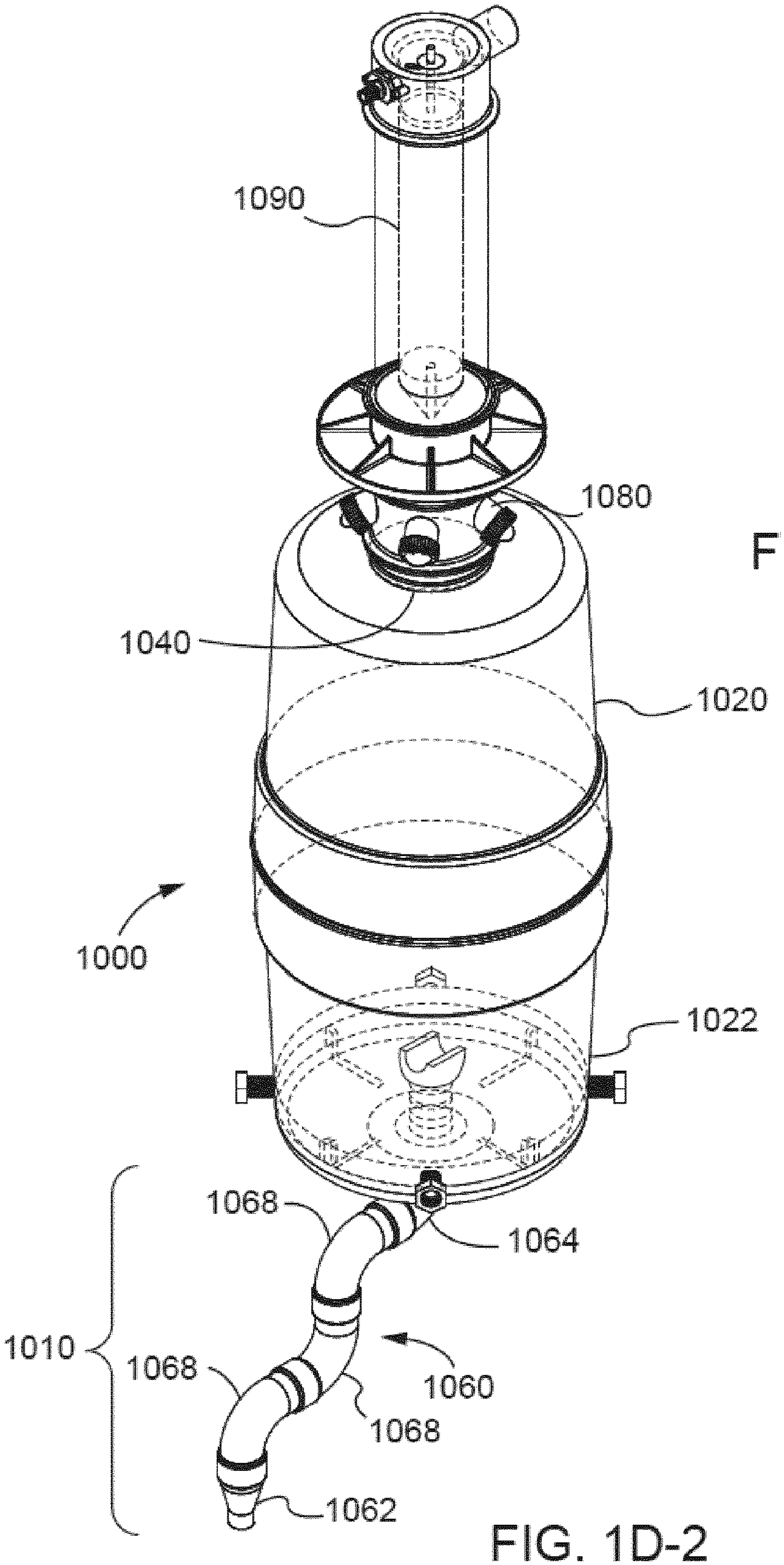
Figure 1E:
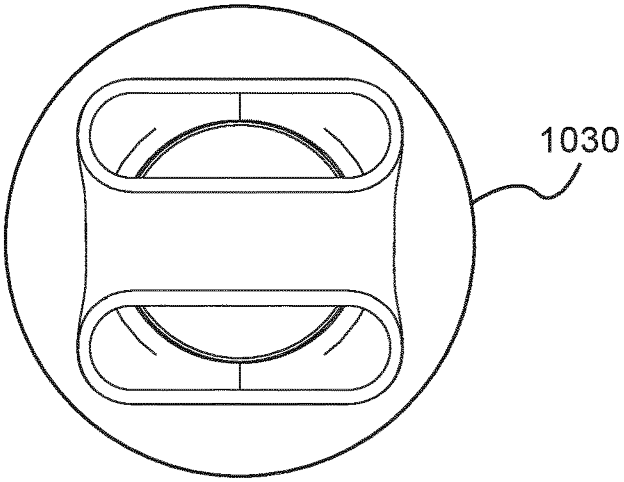
FIG. 1E illustrates an inlet arranged at the base of a drying chamber for a particle generating apparatus according to some embodiments of the disclosure.
Figure 1F:
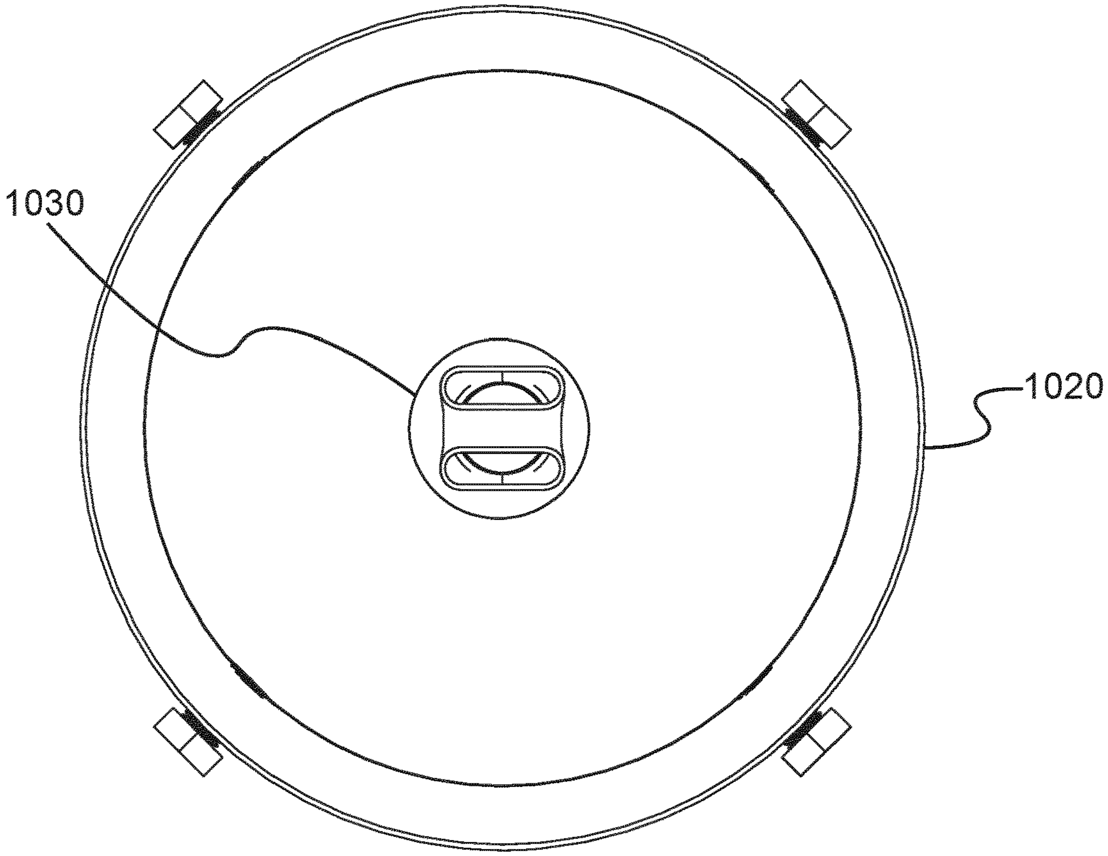
FIG. 1F illustrates a view of a drying chamber and inlet thereof, for a particle generating apparatus according to some embodiments of the disclosure.

In some embodiments, the apparatus further includes a drying chamber 1020, configured to expose the droplet flow to a drying flow so as to produce a dried particle flow having particles of a size and/or mass less than a predetermined threshold size, in some embodiments, 350 nm, 10 and 700 nm, 20 and 600 nm, 30 and 500 nm, 40 and 400 nm, and 50 and 350 nm, and in some embodiments, size ranges therebetween, and configured to direct the dried particle flow with particles of a size lesser than or equal to a predetermined threshold into an area with one or more ionizers. The drying chamber, in some embodiments, includes a drying chamber air inlet 1030 configured to supply air for the drying flow at a regulated flowrate to regulate at least one of the volume of the droplets and volume of dried particles, a fan/pump (may be of the type 9GV0612P1G03) located after the exhaust filter (not shown) configured to provide a constant pressure to the drying flow, a drying chamber outlet 1040, a heater 1050 (e.g., a heating element) configured to regulate a temperature of the drying flow located at a bottom 1022 of the drying chamber, a laminar filter (not shown) located above the heater at the bottom of the drying chamber configured to homogenize the drying flow. The drying chamber 1020 is configured to provide a controlled upward directed flow of the drying flow so as to dry the received droplet flow to form the plurality of dried particles, and droplets over a predetermined size and/or mass travel downward against the drying flow for at least one of collection, and disposal. FIG. 2 is a graph of ionizer voltage versus supply voltage for an ionizer for a particle generating apparatus according to some embodiments of the disclosure. As shown, output voltage flattens out after 10 volts, and preferably, embodiments of the present disclosure utilize 12 volts. In some embodiments, a +/−100 mV supply voltage ripples the output voltage would vary from −4.307 to −4.311 kV. An alternating voltage features the advantage of ionizing the traveling solid particles with positive and negative charge. This results in canceling of the voltage generated by the powder that otherwise would decrease the collection efficiency.

In some embodiments, the apparatus further includes a connector 1060 having a bottom end 1062, a top end 1064, a conduit connecting the bottom end and the second end, and an connector air inlet 1066 arranged on the bottom end; the connector is configured such that the top end 1064 is arranged downstream from the bottom end 1062 and directs the droplet flow into the drying chamber 1020, while droplets larger than a predetermined size fall back (which can be reused, e.g., directed back to the solution container). In some embodiments, the conduit includes at least two turns 1068 forming at least one corresponding S-bend, the top end 1064 includes the connector air outlet (which in some embodiments, corresponds to or otherwise comprises a/the drying chamber inlet) configured to at least one of shape and split the droplet flow into a plurality of flows.

In some embodiments, the apparatus further includes at least one, and in some embodiments, a plurality of ionizers 1080 arranged to expose the particle flow received from the drying chamber via the drying chamber outlet 1040, where each of the ionizers produce an ionized flow of negative ions configured to charge the particles to produce a charged particle flow.

Figure 1G:
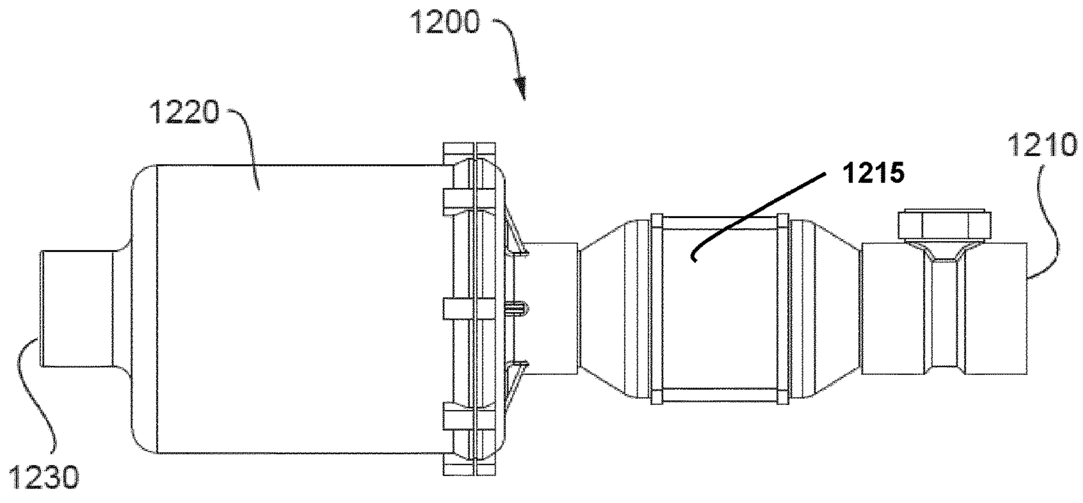
FIG. 1G illustrates a side view of an exhaust assembly for a particle generating apparatus according to some embodiments of the disclosure.
Figure 1H:
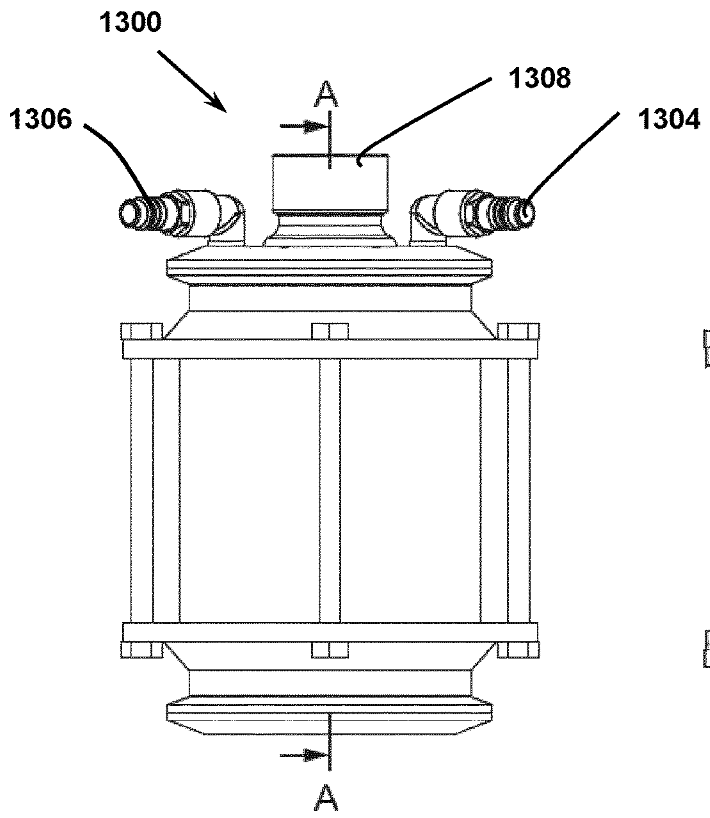
FIG. 1H illustrates a side view of an atomization fuselage for a particle generating apparatus according to some embodiments of the disclosure.
Figure 1I:
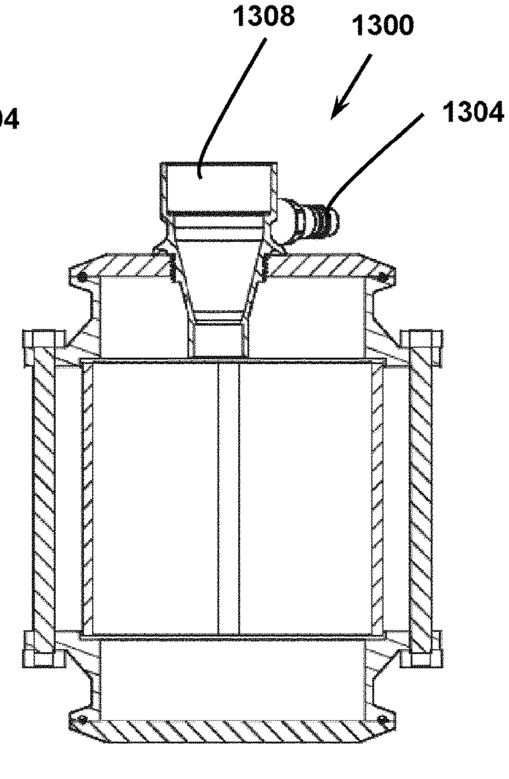
FIG. 1I illustrates a cross-sectional view A-A (see FIG. 1H) of the atomization fuselage of FIG. 1H, for a particle generating apparatus according to some embodiments of the disclosure.
Figure 1J:
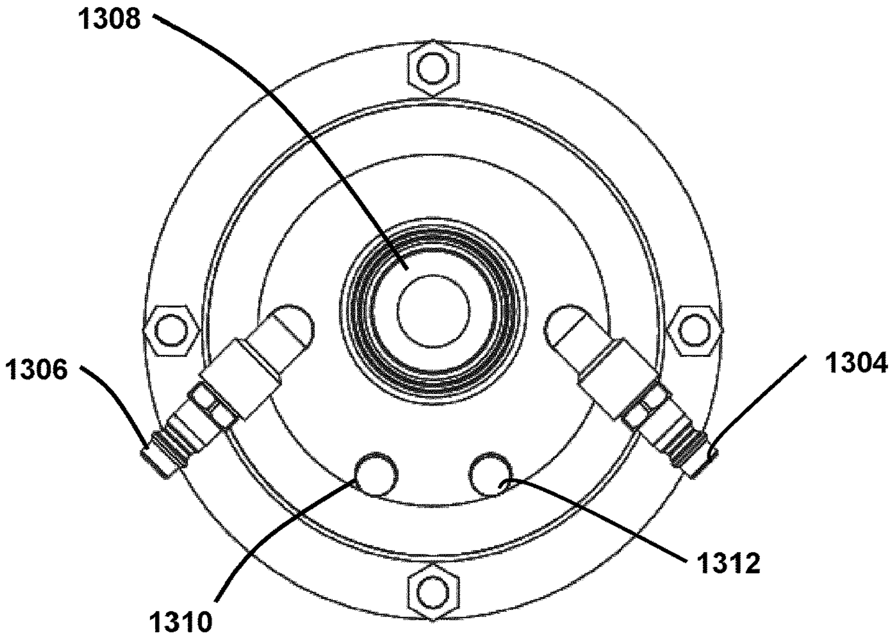
FIG. 1J illustrates a top view of the atomization fuselage of FIG. 1H, for a particle generating apparatus according to some embodiments of the disclosure.
Figure 1K:
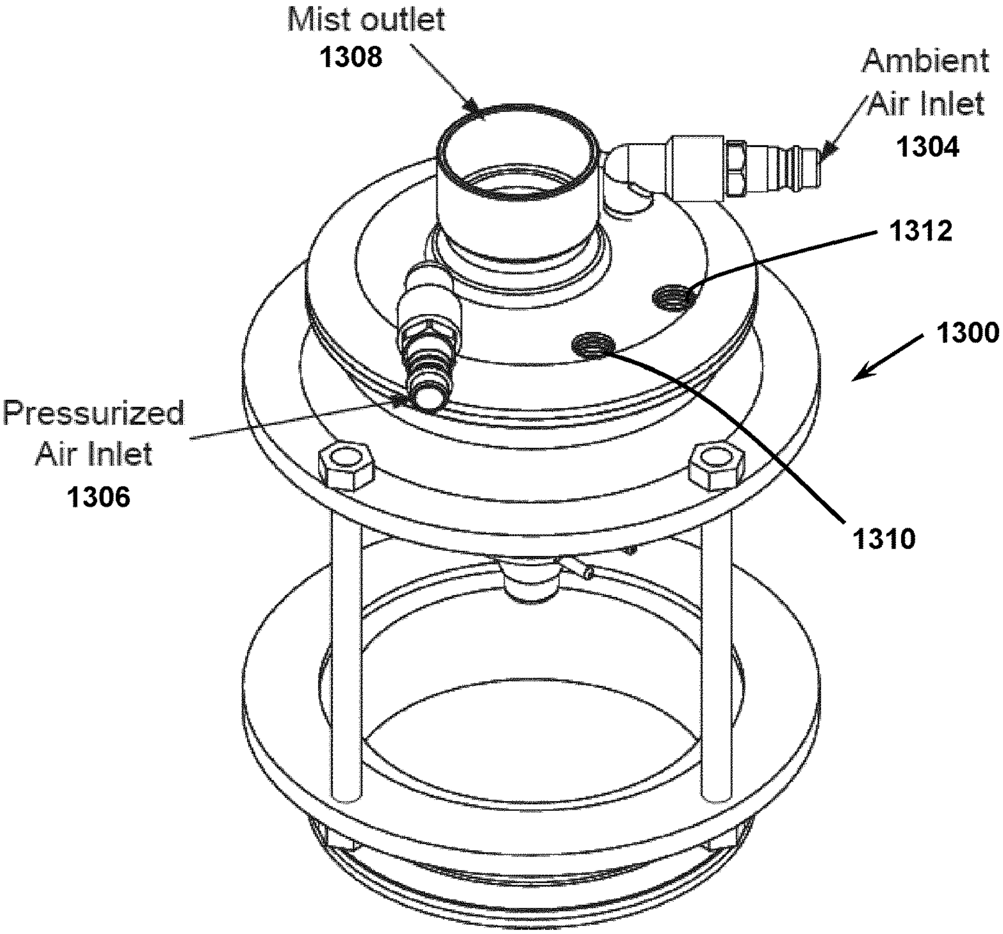
FIG. 1K illustrates a perspective view of the atomization fuselage of FIG. 1H, for a particle generating apparatus according to some embodiments of the disclosure.
Figure 1L:
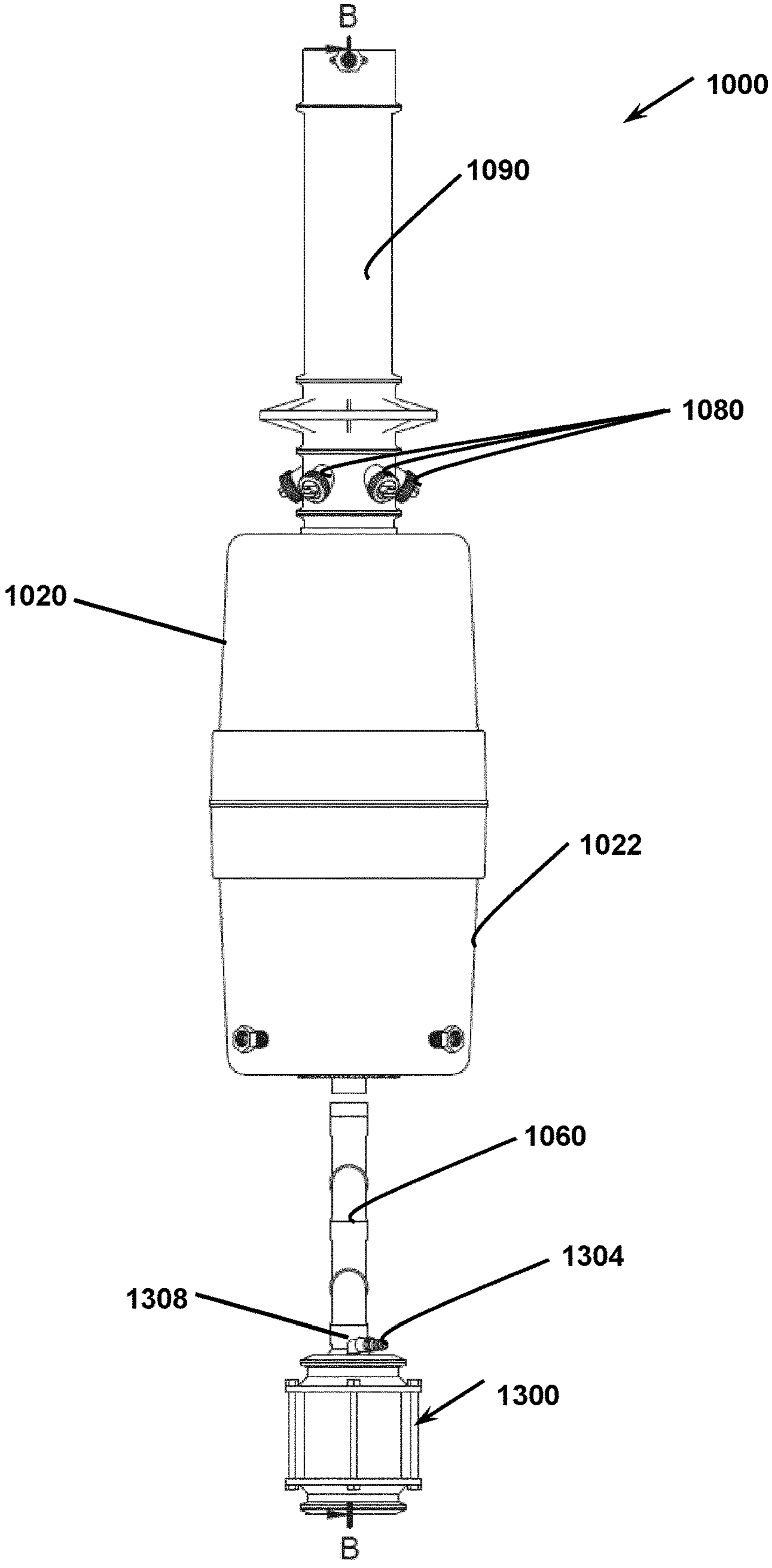
FIG. 1L illustrates another assembled side view of at least a portion of a particle generating apparatus according to some embodiments of the disclosure, including an atomization fuselage.
Figure 1M:
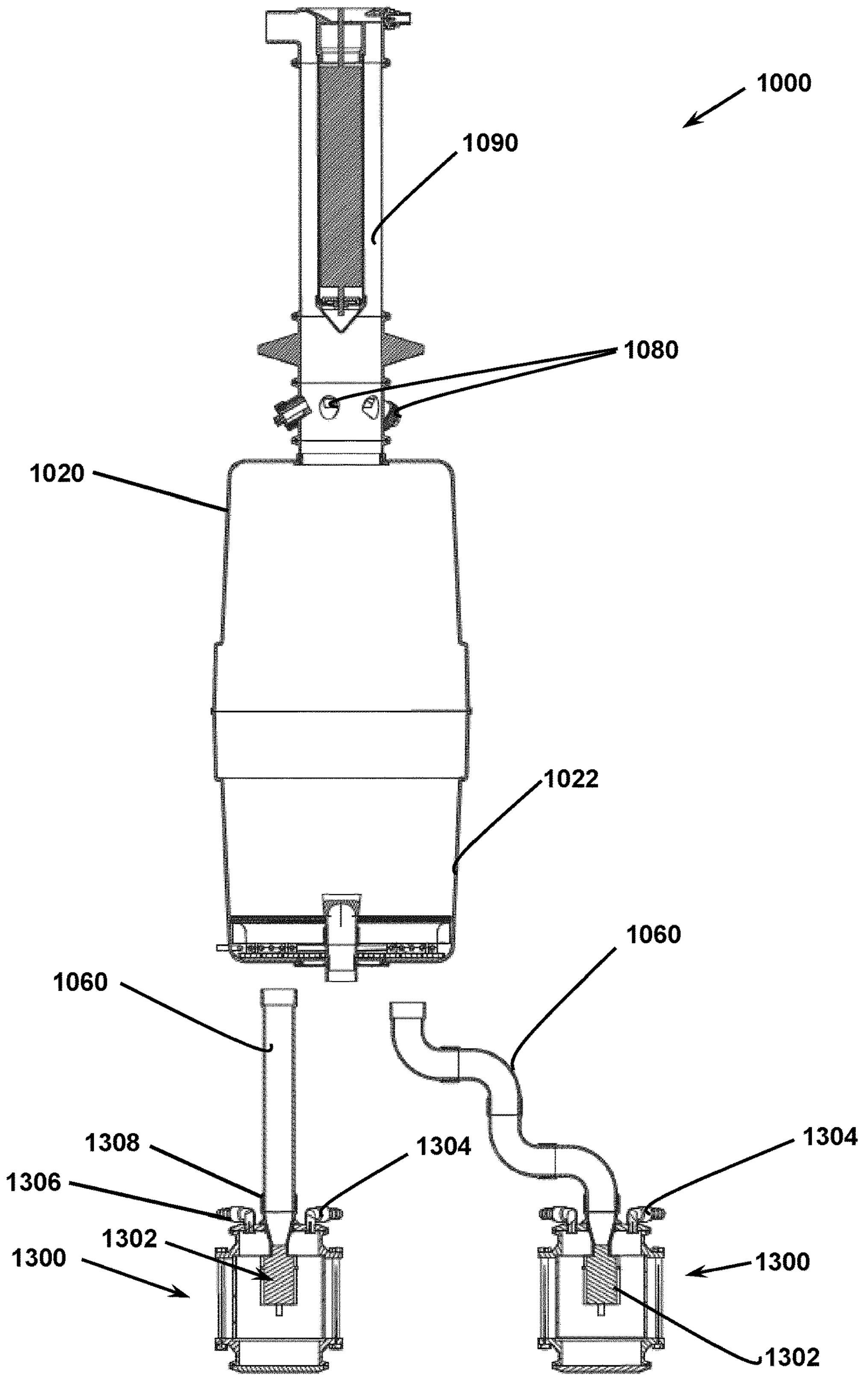
FIG. 1M illustrates a partially assembled, cross-sectional alternate side view, along plane B-B of FIG. 1L, of a particle generating apparatus according to some embodiments of the disclosure, including connectors with atomization means (e.g., nebulizer) and an atomization fuselage.
Figure 1N:
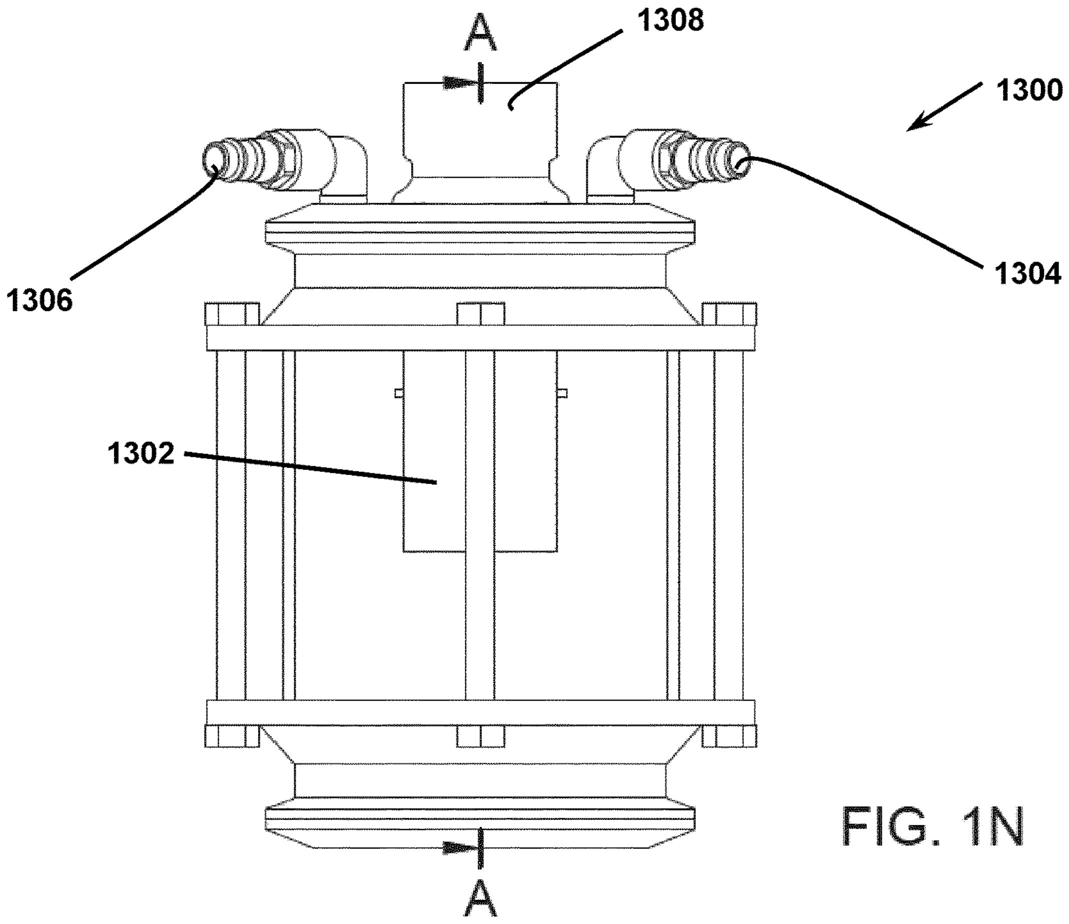
FIG. 1N illustrates another side view of the atomization fuselage of FIG. 1H, including a nebulizer therein, for a particle generating apparatus according to some embodiments of the disclosure.
Figure 1O:
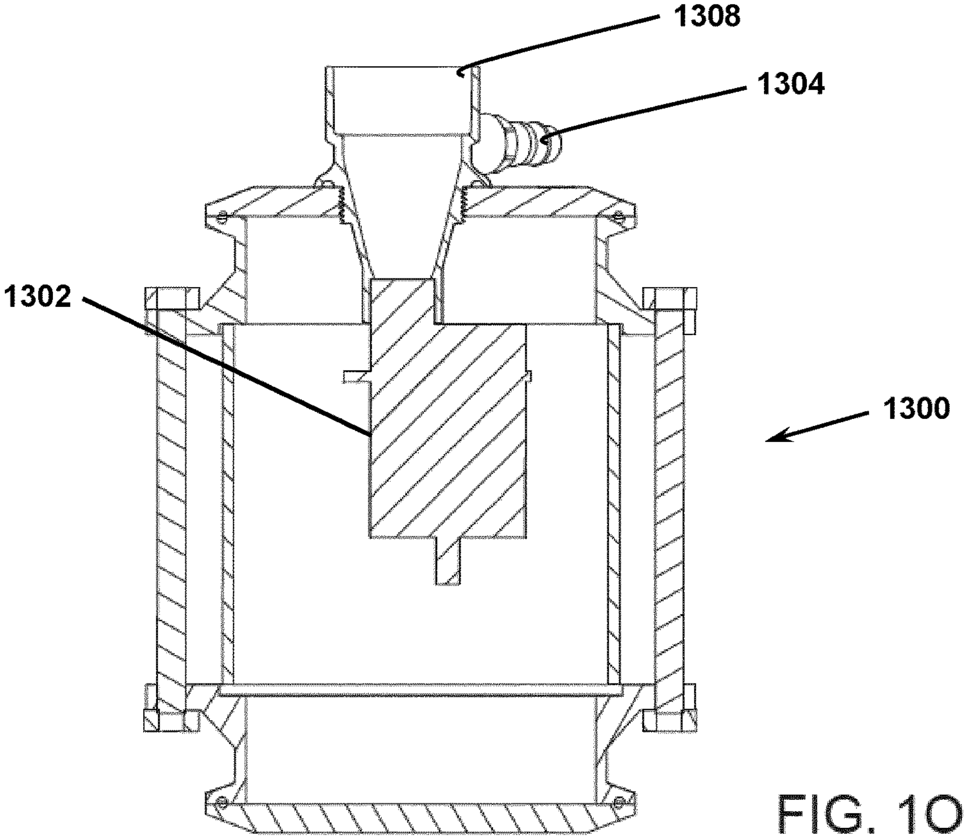
FIG. 1O illustrates another side, cross-sectional view of the atomization fuselage of FIG. 1H (along plane A-A) including a nebulizer therein, for a particle generating apparatus according to some embodiments of the disclosure.
Figure 2:
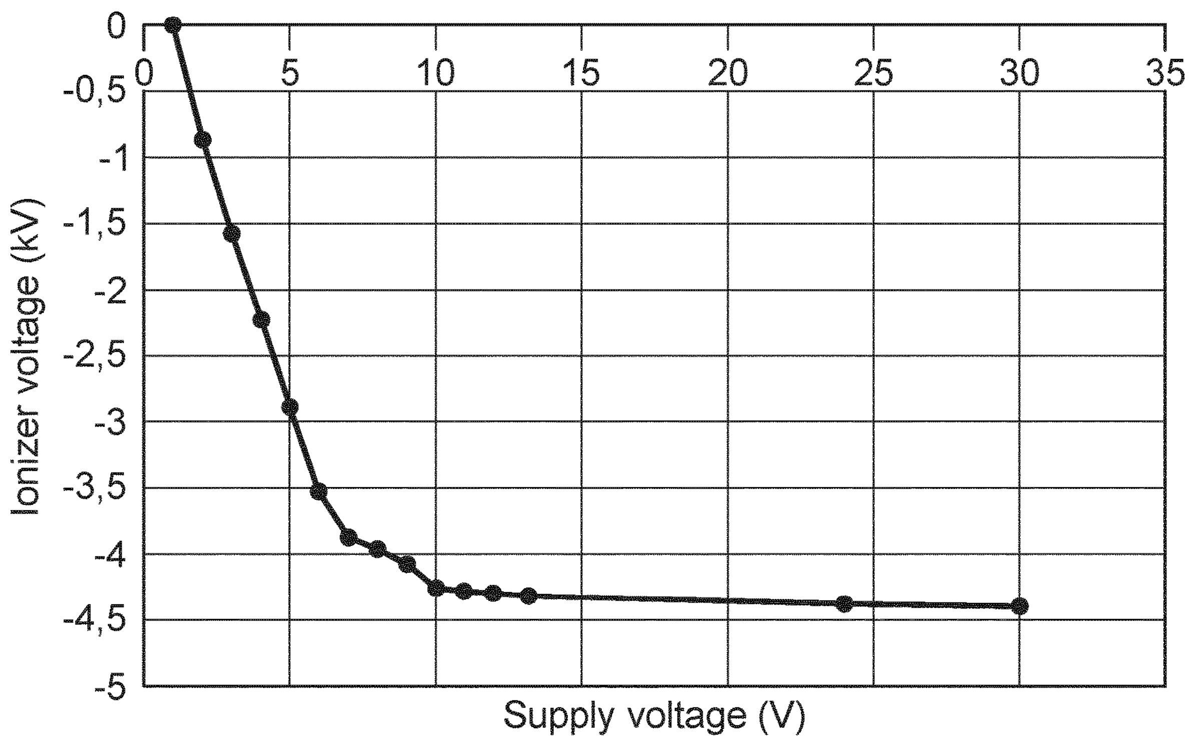

In some embodiments, the apparatus further includes an electrostatic collector 1090 having a predetermined voltage and configured to receive the charged particle flow, an includes a central ground electrode protected by a glass tube, an external cylinder having a wall with a surface at the predetermined voltage, and an electrostatic collector exhaust (which, in some embodiments, can be considered an outlet, as well as in some embodiments, directs/outputs/exhausts remaining flow. The electrostatic collector is configured to deflect the incoming charged particles of the charged particle flow towards the surface of the wall, such that, the particles form a layer thereon. Additionally, the apparatus further includes a filter configured to capture dried particles from the electrostatic exhaust that are not collected in the electrostatic collector, and an apparatus exhaust arranged to exhaust a remaining flow. The electrostatic exhaust, filter, and any other structure to receive remaining flow after the electrostatic collector, can be part of an exhaust assembly, as shown in FIG. 1G. As shown in FIG. 1G, the exhaust assembly 1200, includes an inlet 1210 for receiving a remaining flow from the electrostatic collector, various conduits, connectors and/or fan 1215, and filter housing 1220 (which houses a filter, e.g., HEPA filter), for filtering remaining particles from the received flow, and an exhaust 1230, for exhausting the filtered flow.

In some embodiments, the apparatus includes an electrostatic precipitation system, such as can be found in commercially available electrostatic precipitators, configured to receive the particle flow from the drying chamber and to separate out the solid particles thereof. Additionally, the apparatus further can include a filter configured to capture dried particles from the electrostatic exhaust that are not collected by the electrostatic precipitation system, and an exhaust arranged to exhaust a remaining flow. The exhaust, filter, and any other structure to receive remaining flow after the electrostatic collector, can be part of an exhaust assembly, as shown in FIG. 1G. As shown, the exhaust assembly 1200, includes an inlet 1210 for receiving a remaining flow from the electrostatic collector, various conduits and/or connectors 1215, and filter housing 1220 (which preferably houses a filter, e.g., HEPA filter), for filtering remaining particles from the received flow, and an exhaust 1230, for exhausting the filtered flow.

In some embodiments, a process for producing a population of particles is provided (and in some embodiments, using one and/or another of the apparatuses/systems and devices disclosed herein). In such embodiments, a solution featuring dissolved proteins (for example), of a predetermined concentration, is pumped or otherwise provided to an atomization means (see above). At the atomization means, the solution is atomized. Droplets are generated by atomization form a droplet flow (which may also be referred to as a mist or mist flow) are directed to a connector structure (see above) that selectively separates smaller droplets from larger droplets. In some embodiments, the separation is enhanced by gravity (which may be attained via arrangement of the apparatus, or components thereof, disclosed above according to some embodiments). Accordingly, large droplets of greater than a particular size (and/or mass) flow back into the solution to be reused (e.g., can be directed back to the atomization means or contain for storing the solution).

The droplet flow with smaller particles travels up to an inlet (which may also be referred to as an orifice or a nozzle) of a drying chamber (see above). In the drying chamber, a controlled upward directed flow of hot air or gas is sued to evaporate the droplets, where, as a result, small particles (e.g., of the dissolved molecule, e.g., a protein) are formed and continue to travel upstream in the apparatus. Since the airflow moves the particles against gravity (in some embodiments), particles (and/or droplets) greater than a threshold size and/or mass that are too heavy to be retained in the upward airflow, fall down and be discarded from a final product.

In some embodiments, the dried particles travel through a conduit featuring one or multiple ionizers that provide a flow of negative ions charges to the dried particles thereby charging the particles. The charged particles then travel into an electrostatic collector (see above), where particles are deflected toward a surface of a wall of a component of the electrostatic collector where the dried particles (at least a portion, and in some embodiments, most of the particles, and in some embodiments all or substantially all of the deflected, dried particles) collect thereon forming a layer. Remaining particles which do not form part of the layer of collected particles, can continue traveling upstream and exhausted into a filtration device (e.g., HEPA filter), via, for example, an exhaust assembly (see FIG. 1G).

In some embodiments, computer modeling, and more specifically, computational fluid dynamics (CFD) is used (via a processor/computer) to improve particle yield (i.e., mg out/mg in), PSD, and particle quality. Accordingly, in some such embodiments, CFD is used to describe a two phase or three phase flow of fluid (gas/fluid solid particulate) in systems (according to the disclosed embodiments). To this end, using CFD, according to some embodiments, aids in identifying and engineering against vortexes (for example, for improved yield) in places where solution/particles (e.g., API) cannot be recovered. For example, in some embodiments, CFD functionality is validated/calibrated for specific conditions in the particle generating system (according to some embodiments) by using light sheet enabled particle image velocimetry, such that, particles provide natural entities which can be followed. Accordingly, this approach, in some embodiments, permits achieving a smaller size distribution spread, increase production rate and yield, since turbulent areas can be engineered away.

For example, in some embodiments, particles production can be modeled based on density or density gradient, and/or minimizing a change of line time by minimizing build-up of particulates and residue in hard to clean areas (e.g., nooks and crannies) of the apparatus/system.

As shown in FIGS. 1H-1K, the system, according to some embodiments, can include an atomization fuselage 1300 for housing the atomization means. The fuselage can be configured as an enclosed container, and preferably, is airtight/sealed. A portion (e.g., a side, an end) can include (or can be included on different portions) a pressurized air inlet 1306, an ambient air inlet 1304, and an outlet 1308 (which is configured to exhaust the droplet flow from the atomization means), a solution inlet 1310 and a solution outlet 1312. Clean air and/or other gas (e.g., nitrogen) can be introduced into the fuselage at a controlled rate (corresponding to "ambient air"), creating a flow which carries the droplet flow out of the atomization means. While many commercially available nebulizers rely on the venturi effect to suck in surrounding air for carrying the mist, the fuselage allows us to precisely regulate the mist composition and velocity through the ambient air flow, as well as controlling the cleanliness of the ambient air.

CFD functionality can, in some embodiments, provide a process to calibrate, e.g., with a lookup table, the drying air flow, allowing particle image velocimetry to be used in a real-time feedback loop to keep flow in an optimal mode (allowing for achievement of predetermined goals). Accordingly, the less stochasticity in the flow, the more/tighter control of the particle size, and thus, particle sizes can be optimized in a deterministic fashion.

Figure 6A:
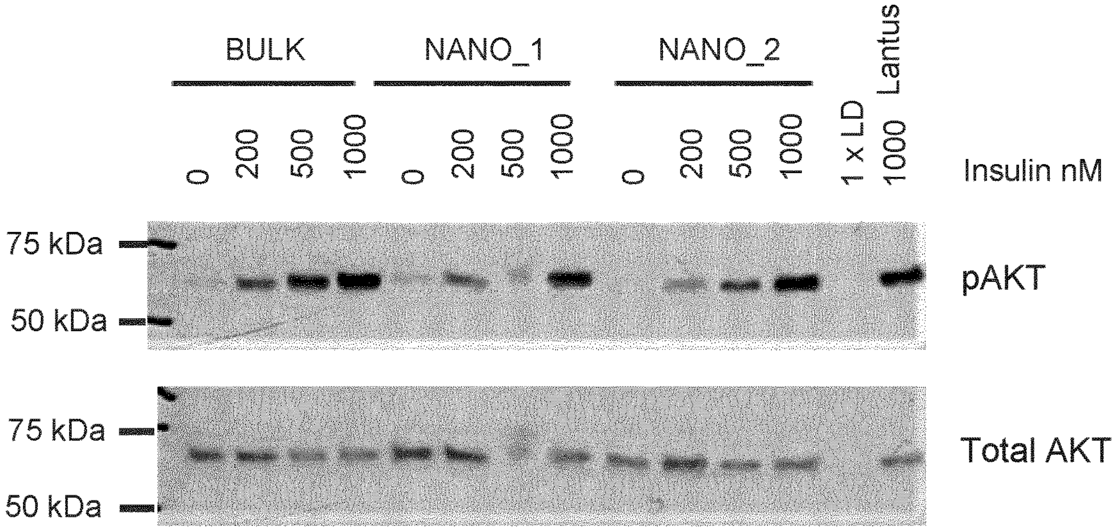
FIG. 6A is an immunoblot for in vitro activity determination of the newly produced insulin samples produced with a particle generating apparatus according to some embodiments of the present disclosure.
Figure 6B:
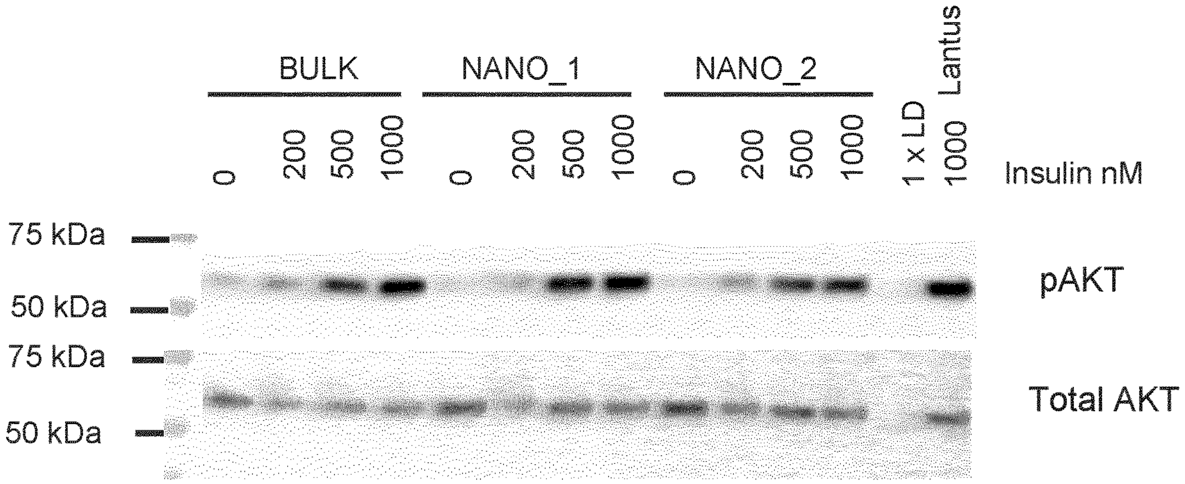
FIG. 6B is an immunoblot for in vitro activity determination of the 1-month-old, processed insulin samples produced with a particle generating apparatus according to some embodiments of the present disclosure.

Particles produced, according to some embodiments, enable the production of improved particles (see FIG. 5C), for example, human insulin. In one example, human insulin particles (Sigma 91077C) were produced using a method and system for a particle producing apparatus according to some embodiments, and performed at between 20-80° C. (as well as other ranges as noted in the summary section). After collection of the produced particles, the powder was dissolved in 1% acetic acid, subsequently diluted into PBS and the activity was assayed using human hepatoblastoma HepG2 cell-line (ATCC HB-8065). Accordingly, HepG2 cells were kept in serum-free medium for 3 hours, and induced thereafter for 30 minutes with 200 nm, 500 nm, or 1000 nm unprocessed bulk insulin (BULK) or nanoformed insulin (NANO_1 and NANO_2). 1000 nm Lantus Glargine (Sanofi) was used as a positive control for the assay (see FIG. 6A). After induction, the cells were washed with cold PBS and lysed in extraction buffer (TBS, 10% glycerol, 1% TritonX-100, 1% Nonidet P-40, 2 mM EDTA, and Mini complete protease inhibitor cocktail (Roche). To assess the activation level of insulin receptor, a downstream signaling molecule AKT was chosen as an out read. The samples were immunoblotted using pAKT (Cell signaling 9271) and AKT (Cell Signaling 9272). The bulk and the nanoformed samples were then kept at +4 C for 1 month, thereafter the activity assay on HepG2 cells was repeated using these samples. Cell lysates were immunoblotted again with antibodies against pAKT and AKT, to assess the level of retained activity of the 1-month-old samples (see FIG. 6B).

Figure 7A:
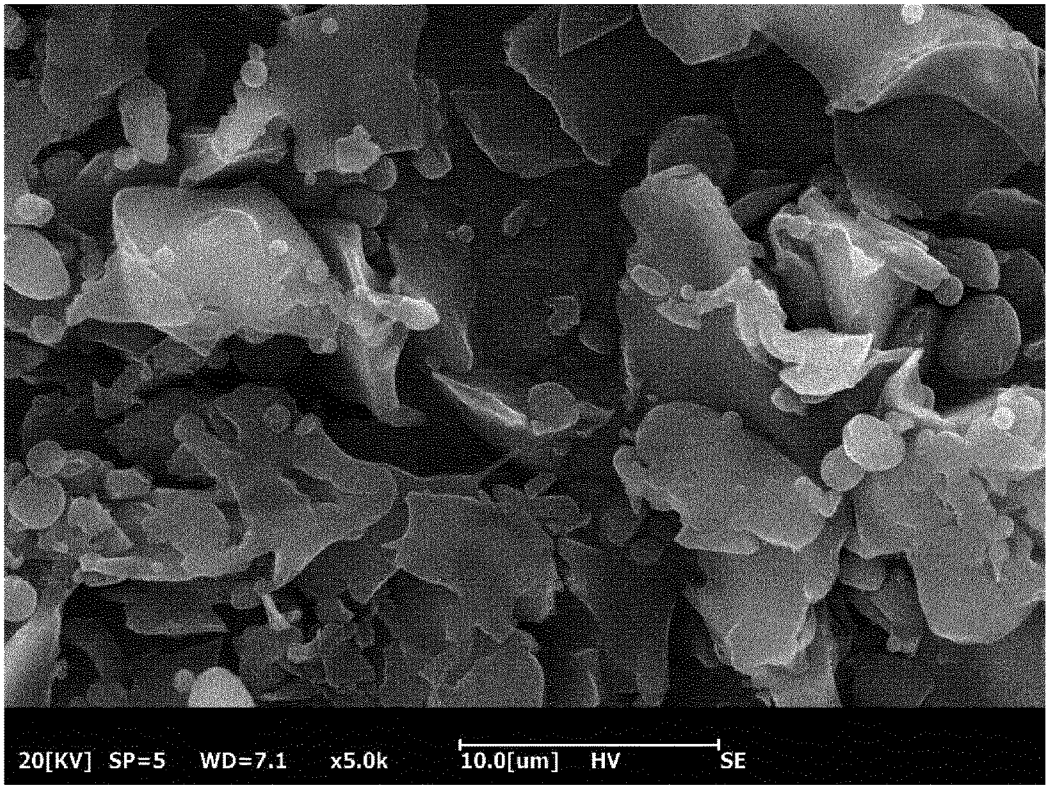
FIG. 7A is an image of unprocessed, bulk lactic dehydrogenase before use in a particle generating apparatus according to some embodiments of the present disclosure.
Figure 7B:
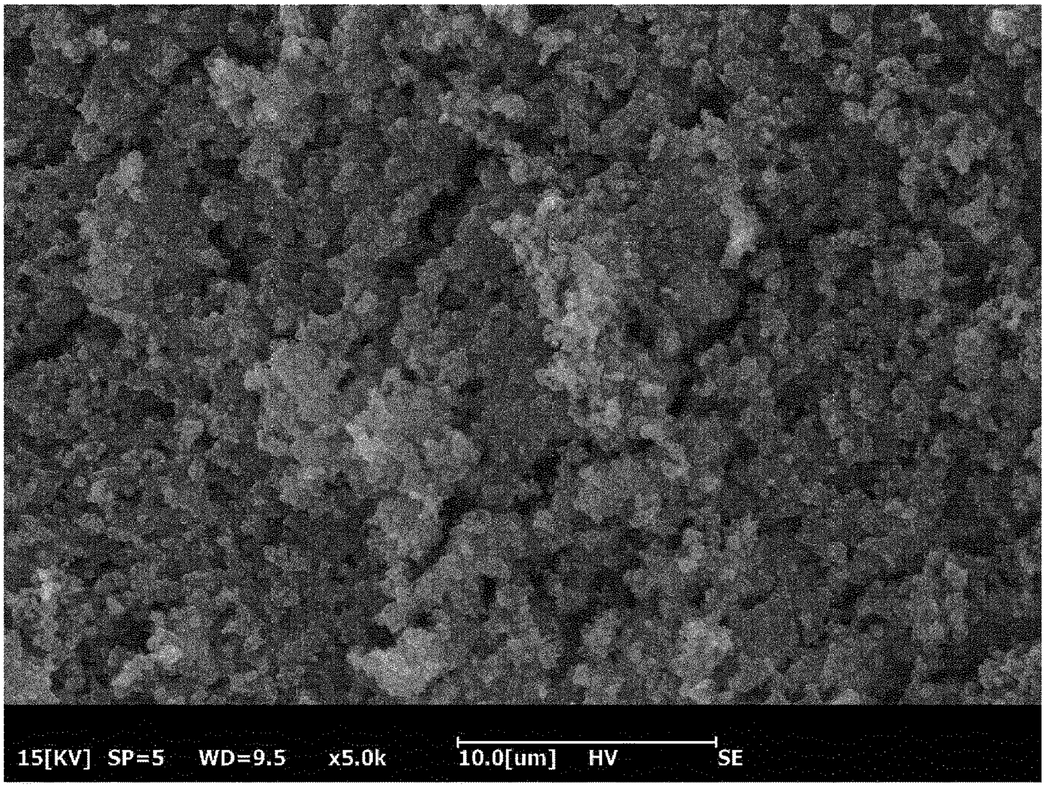
FIG. 7B is an image of resulting particles of lactic dehydrogenase produced in a particle generating apparatus according to some embodiments of the present disclosure.
Figure 7C:
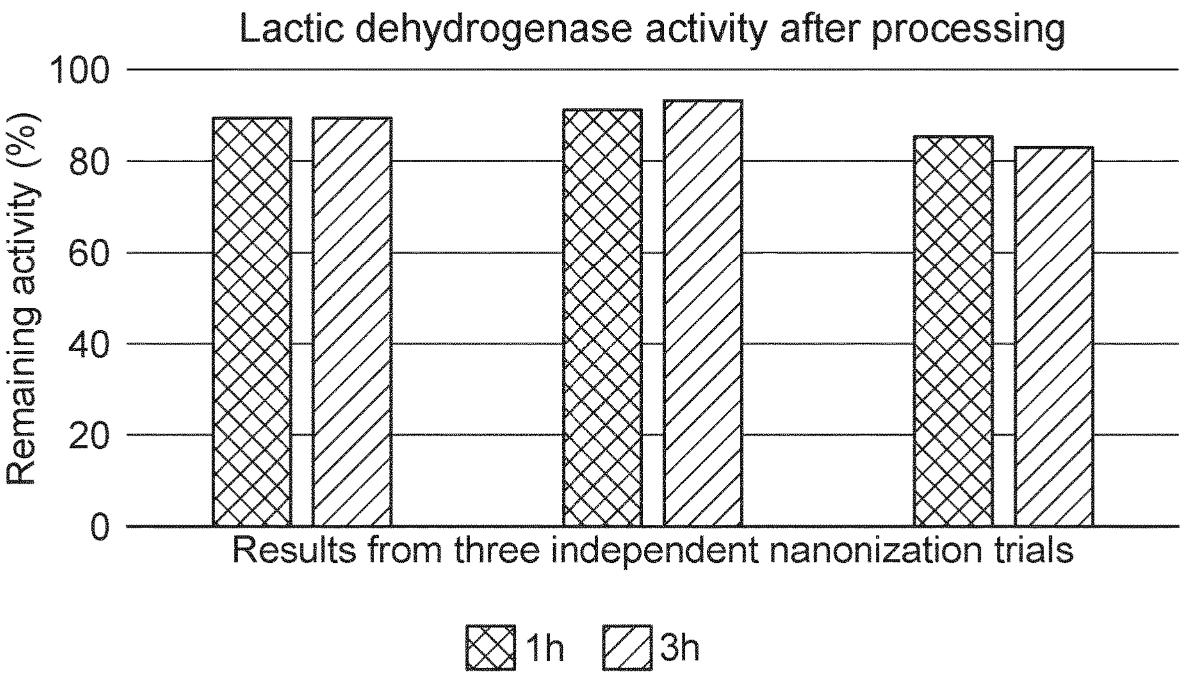
FIG. 7C is a graph illustrating percentage of remaining activity lactic dehydrogenase particles produced according to embodiments of the present disclosure, after processing in three trials, at both 1 hour and 3 hour timepoints.

Similarly, Lactic Dehydrogenase (LDH, Sigma L1254) was nanoformed using a system and method according to some embodiments, at 20-80° C. (see FIGS. 7A-7B). After collection, the resulting powder was dissolved in PBS (Gibco 14189-144) and the activity was assayed using LDH Activity Assay Kit (Sigma-Aldrich MAK006) according to the manufacturer's instructions using a multimode microplate reader (Perkin Elmer, Victor Nivo). Protein concentration of the initial feed solution as well as the solution containing the dissolved nanopowder was measured (Thermo Scientific, μDropTM Plate) and used for normalizing the activity assay results. FIG. 7C shows remaining LDH activity from three independent trials, followed by three independent activity assays. Remaining activity was calculated as the activity of the dissolved nanopowder (at both 1 hour and 3 hours after dissolution) as a percentage of the initial LDH activity of the feed solution. The average remaining activities were 88.4% (1 h) and 88.3% (3 h).

Figure 8A:
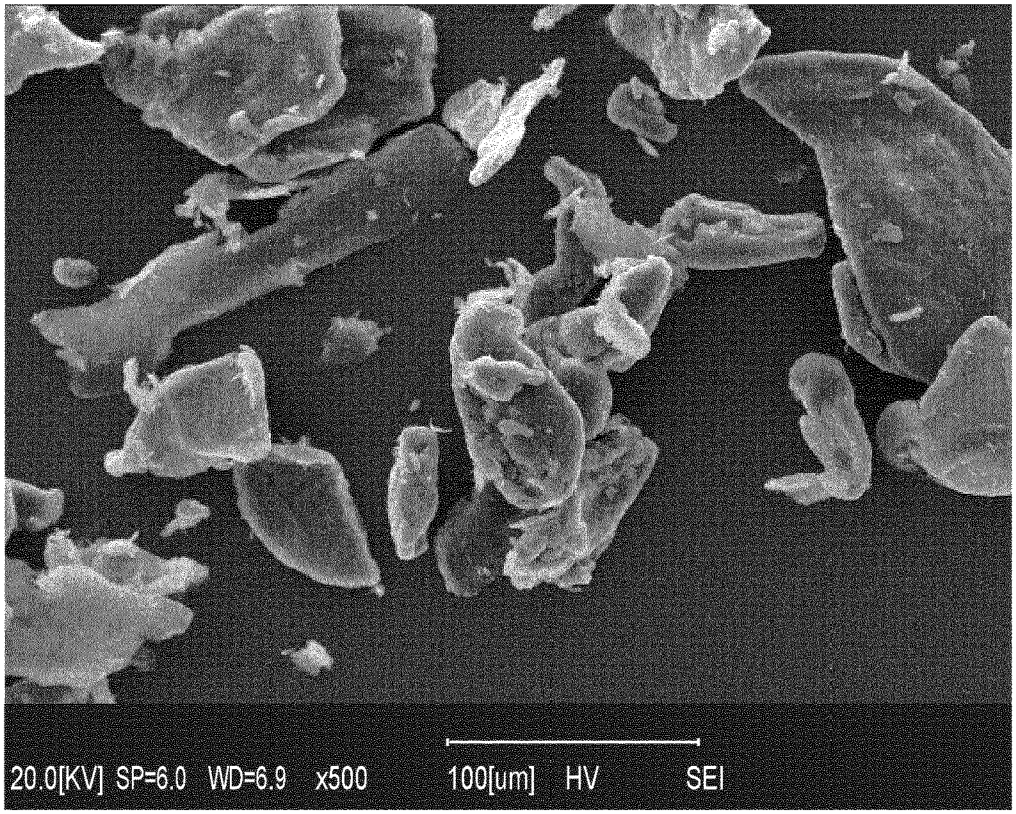
FIG. 8A is an image of unprocessed, bulk chitosan before use in a particle generating apparatus according to some embodiments of the present disclosure.
Figure 8B:
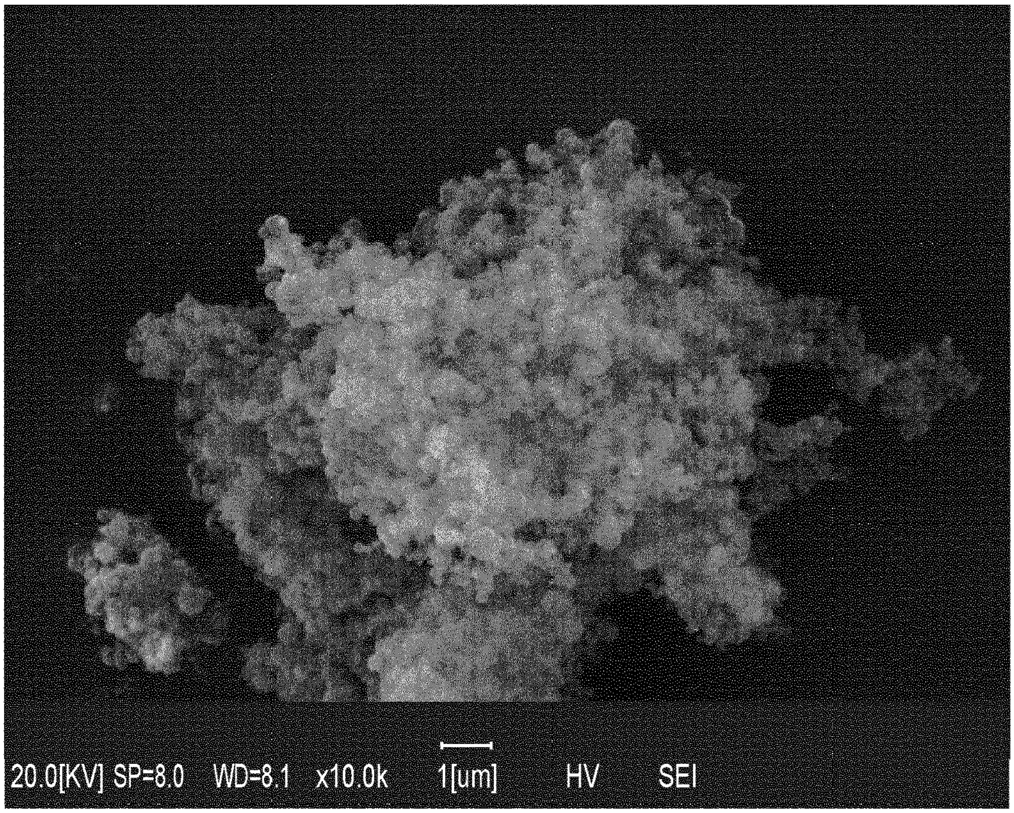
FIG. 8B is an image of resulting particles of chitosan produced in a particle generating apparatus according to some embodiments of the present disclosure.

FIGS. 8A-8B are images of respective bulk product and particles produced by system and method embodiments according to some embodiments of the disclosure. Specifically, FIG. 8A is an image of unprocessed chitosan for use in a particle generating apparatus according to some embodiments of the present disclosure, and FIG. 8B is an image of resulting particles of chitosan produced in a particle generating apparatus according to some embodiments of the present disclosure.

While various inventive embodiments have been described and illustrated herein, those of ordinary skill in the art will readily envision a variety of other means, steps, and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant only to be examples and that actual parameters, dimensions, materials, and configurations will depend upon the specific application or applications for which the inventive teachings is/are used. Those skilled in the art will also recognize, or be able to ascertain using no more than routine experimentation, many equivalents to the specific inventive embodiments described herein. It is, therefore, to be understood that the foregoing disclosed embodiments are presented by way of example only and that, within the scope of claims supported by the present disclosure (including equivalents thereto), inventive embodiments may be practiced otherwise than as specifically described and claimed.

Some of the inventive embodiments of the present disclosure are directed to each individual feature, system, article, material, kit, method, and step, described herein. In addition, any combination of two or more such features, systems, articles, materials, kits, methods, and steps, if such features, systems, articles, materials, kits, methods, and steps, are not mutually inconsistent, is included within the inventive scope of the present disclosure. Some embodiments disclosed herein may also be combined with one or more features, as well as complete systems, devices or methods of other embodiments (as well as known systems, devices, or methods) to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, as shown above, various inventive concepts may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The terms "can" and "may" are used interchangeably in the present disclosure, and indicate that the referred to element, component, structure, function, functionality, objective, advantage, operation, step, process, apparatus, system, device, result, or clarification, has the ability to be used, included, or produced, or otherwise stand for the proposition indicated in the statement for which the term is used (or referred to) for a particular embodiment(s).

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

What is currently claimed:

1. A method of producing a population of particles comprising:

atomizing a solution featuring a dissolved predetermined molecule of a predetermined concentration to produce a plurality of droplets in a droplet flow; separating the droplets of less than or equal to a threshold size and/or mass in the droplet flow via at least one of:

gravity and upward flow along a connector, wherein droplets greater than the threshold size and/or mass flow back against the upward flow and are collected for re-atomization or discarded, and electrostatic separation;

directing the droplet flow containing the droplets of less than the threshold size into one or more elevated temperature drying flows, wherein the elevated temperature drying flows provide a controlled upward directed flow of air or gas so as to evaporate the droplets to produce a plurality of dried particles in a dried particle flow, wherein particles and/or droplets having a size and/or mass greater than a threshold amount too heavy to be retained in the dried particle flow, fall down and are discarded (or collected/returned);

charging the dried particles in the dried particle flow with a temporally and/or spatially predetermined or preprogrammed flow of negative ions establishing a charged particle flow;

and collecting the dried particles.

2. The method of claim 1, wherein the size of a dried particle is selected from the group consisting of between: 10 and 700 nm, 20 and 600 nm, 30 and 500 nm, 40 and 400 nm, and 50 and 350 nm.

3. The method of claim 1, wherein the predetermined molecule comprises an active pharmaceutical ingredient (API).

4. The method of claim 1, wherein the drying flow is at a predetermined temperature.

5. The method of claim 1, wherein the elevated temperature drying flow is provided at a substantially constant pressure between 0.0 to −0.30 mbar relative to ambient pressure.

6. The method of claim 1, wherein the particles are charged via at least one ionizer having a specific output voltage.

7. The method of claim 1, wherein a flowrate of are provided for the droplet flow to at least aid in propelling the plurality of droplets is between 5 and 20 L/min.

8. The method of claim 1, wherein the predetermined dissolved molecule concentration ranges from 0.1 to 20 g/L.

9. The method of claim 1, wherein a flowrate of the elevated temperature drying flow ranges from 50 to 200 L/min.

10. The method of claim 1, wherein the molecule is selected from the group consisting of: a protein, a nucleic acid, a carbohydrate, a small molecule embedded in a protein, an excipient, and a salt.

11. The method of claim 1, wherein at least one of the droplet flow, the drying flow, the dried particle flow, and the charged particle flow comprise corresponding airflows.

12. The method of claim 1, wherein collecting comprises deflecting the charged particle flow via an electrostatic collection device comprising one or more elements onto a surface for collection thereof, wherein the charged particle flow is deflected onto the surface in a predetermined or preprogrammed pattern.

13. The method of claim 1, wherein the temperature of the elevated temperature drying flows is between 20 and 80 degrees C.

14. A method of producing a population of particles comprising:

atomizing a solution featuring a dissolved predetermined molecule of a predetermined concentration to produce a plurality of droplets in a droplet flow, wherein the predetermined molecule comprises an active pharmaceutical ingredient (API) or an excipient; separating the droplets of less than or equal to a threshold size and/or mass in the droplet flow via at least one of:

gravity and upward flow along a connector, wherein droplets greater than the threshold size and/or mass flow back against the upward flow and are collected for re-atomization or discarded, and electrostatic separation;

directing the droplet flow containing the droplets of less than the threshold size into one or more elevated temperature drying flows, wherein the elevated temperature drying flows provide a controlled upward directed flow of air or gas so as to evaporate the droplets to produce a plurality of dried particles in a dried particle flow, wherein particles and/or droplets having a size and/or mass greater than a threshold amount too heavy to be retained in the dried particle flow fall down and are discarded (or collected/returned);

and collecting the dried particles.

15. The method of claim 14, wherein the size of a dried particle is selected from the group consisting of between: 10 and 700 nm, 20 and 600 nm, 30 and 500 nm, 40 and 400 nm, and 50 and 350 nm.

16. The method of claim 14, wherein the drying flow is at a predetermined temperature.

17. The method of claim 14, wherein the elevated temperature drying flow is provided at a substantially constant pressure between 0.0 to −0.30 mbar relative to ambient pressure.

18. The method of claim 14, wherein a flowrate of are provided for the droplet flow to at least aid in propelling the plurality of droplets is between 5 and 20 L/min.

19. The method of claim 14, wherein the predetermined dissolved molecule concentration ranges from 0.1 to 20 g/L.

20. The method of claim 14, wherein a flowrate of the elevated temperature drying flow ranges from 50 to 200 L/min.

21. The method of claim 14, wherein the molecule is selected from the group consisting of: a protein, a nucleic acid, a carbohydrate, a small molecule embedded in a protein, an excipient, and a salt.

22. The method of claim 14, wherein at least one of the droplet flow, the drying flow, and the dried particle flow, comprise corresponding airflows.

23. The method of claim 14, wherein the temperature of the elevated temperature drying flows is between 20 and 80 degrees C.

* * * * *